(12) United States Patent
Hill et al.

(10) Patent No.: US 9,279,085 B2
(45) Date of Patent: Mar. 8, 2016

(54) METHOD FOR THE PRODUCTION OF MONOFUNCTIONALIZED DIALKYLPHOSPHINIC ACIDS, ESTERS AND SALTS, AND USE THEREOF

(75) Inventors: Michael Hill, Cologne (DE); Harald Bauer, Kerpen (DE); Werner Krause, Huerth (DE); Martin Sicken, Cologne (DE)

(73) Assignee: Clariant Finance (BVI) Limited, Tortola (VG)

( * ) Notice: Subject to any disclaimer, the term of this patent is extended or adjusted under 35 U.S.C. 154(b) by 515 days.

(21) Appl. No.: 13/140,555

(22) PCT Filed: Oct. 6, 2009

(86) PCT No.: PCT/EP2009/007144
§ 371 (c)(1),
(2), (4) Date: Jun. 17, 2011

(87) PCT Pub. No.: WO2010/069420
PCT Pub. Date: Jun. 24, 2010

(65) Prior Publication Data
US 2011/0251315 A1 Oct. 13, 2011

(30) Foreign Application Priority Data
Dec. 19, 2008 (DE) .................. 10 2008 064 003

(51) Int. Cl.
| C07F 9/02 | (2006.01) |
|---|---|
| C07F 9/22 | (2006.01) |
| C07F 9/28 | (2006.01) |
| C08K 5/53 | (2006.01) |
| C09K 21/12 | (2006.01) |
| C07F 9/30 | (2006.01) |
| C07F 9/32 | (2006.01) |
| C08K 5/5313 | (2006.01) |

(52) U.S. Cl.
CPC .............. C09K 21/12 (2013.01); C07F 9/301 (2013.01); C07F 9/3211 (2013.01); C08K 5/5313 (2013.01)

(58) Field of Classification Search
None
See application file for complete search history.

(56) References Cited

U.S. PATENT DOCUMENTS

| 3,345,432 A | 10/1967 | Gillham et al. |
|---|---|---|
| 3,784,638 A | 1/1974 | Lambert |
| 3,875,263 A | 4/1975 | Herwig et al. |
| 3,939,050 A | 2/1976 | Kleiner et al. |
| 3,941,752 A | 3/1976 | Kleiner et al. |
| 3,962,194 A | 6/1976 | Bollert et al. |
| 4,001,352 A | 1/1977 | Kleiner et al. |
| 4,035,343 A | 7/1977 | Bollert et al. |
| 4,069,245 A | 1/1978 | Dursch et al. |
| 4,069,247 A | 1/1978 | Kleiner |
| 4,079,049 A | 3/1978 | Ramsay et al. |
| 4,168,267 A | 9/1979 | Petrillo |
| 4,235,991 A | 11/1980 | Digiacomo |
| 4,337,201 A | 6/1982 | Petrillo |
| 4,374,131 A | 2/1983 | Petrillo |
| 4,381,297 A | 4/1983 | Karanewsky et al. |
| 4,427,665 A | 1/1984 | Karanewsky et al. |
| 4,555,506 A | 11/1985 | Karanewsky et al. |
| 4,594,199 A | 6/1986 | Thottathil et al. |
| 4,602,092 A | 7/1986 | Thottathil et al. |
| 4,634,689 A | 1/1987 | Witkowski et al. |
| 5,013,863 A | 5/1991 | Baylis et al. |

(Continued)

FOREIGN PATENT DOCUMENTS

| AT | 243952 | 12/1965 |
|---|---|---|
| DE | 1494922 | 6/1969 |

(Continued)

OTHER PUBLICATIONS

Smith, Michael B.; March's Advanced Organic Chemistry—Reactions, Mechanisms, and Structure (6th Edition), 2007) March, Jerry 2007 John Wiley & Sons pp. 1813-1814.*
Montchamp et al., J. Organomet. Chem. 690 (2005), 2388-2406.*
Kielbasinski et al., Tetrahedron Asymmetry 13 (2002) 735-738.*
PCT International Search Report for PCT/EP2009/007145, mailed Jan. 25, 2010.
English Translation of the PCT International Preliminary Report on Patentability PCT/EP2009/007145 mailed Jun. 30, 2011.
English abstract for JP 05230085, Sep. 7, 1993.
Russian Journal of General Chemistry (translation of Zhurnal Obschchei Khimii), 74(6) pp. 864-872; XP002561442 (2004).
PCT International Search Report for PCT/EP2009/007123, mailed Jan. 29, 2010.

(Continued)

*Primary Examiner* — Susannah Chung
*Assistant Examiner* — Robert T Butcher
(74) *Attorney, Agent, or Firm* — Anthony A. Bisulca

(57) ABSTRACT

The invention relates to a method for producing monofunctionalized dialkylphosphinic acids, esters, and salts, characterized in that a phosphinic acid source (I) is reacted with olefins (IV) in the presence of a catalyst A to obtain an alkylphosphonous acid, the salt or ester thereof, whereupon said alkylphosphonous acid, the salt or ester (II) thereof is reacted with compounds containing C=C, C=O, or C=N double bonds to obtain compounds of type (III), wherein $R^1$, $R^2$, $R^3$, $R^4$, $R^5$, $R^6$ are identical or different from each other and independently represent, inter alia, H, $C_1$-$C_{18}$-alkyl, $C_6$-$C_{18}$-aryl, $C_6$-$C_{18}$-aralkyl, X represents, inter alia, H, $C_1$-$C_{18}$-alkyl, $C_6$-$C_{18}$-aryl, and/or Mg, Ca, Al, Sb, Sn, Ge, Ti, Fe, Zr, Zn, Ce, Bi, Sr, Mn, Cu, Ni, Li, Na, K, H, and wherein A represents OH, $NH_2$, NHR, $NR^2$, or O—CO—$R^8$, and W represents a mineral acid, carboxylic acid, Lewis acid, or organic acid, wherein n is a whole or a fractional number from 0 to 4, and catalyst A represents transition metals and/or transition metal compounds and/or catalyst systems composed of a transition metal and/or a transition metal compound and at least one ligand. The use of said dialkylphosphonic acids, esters, and salts is also disclosed.

12 Claims, No Drawings

(56) References Cited

U.S. PATENT DOCUMENTS

| | | | |
|---|---|---|---|
| 5,153,347 A | 10/1992 | Lloyd | |
| 5,190,933 A * | 3/1993 | Baylis et al. | 514/114 |
| 5,190,934 A | 3/1993 | Mickel et al. | |
| 5,229,379 A | 7/1993 | Marescaux et al. | |
| 5,391,743 A | 2/1995 | Ebitino et al. | |
| 5,407,922 A | 4/1995 | Marescaux et al. | |
| 5,545,631 A | 8/1996 | Marescaux | |
| 5,739,123 A | 4/1998 | Norcini et al. | |
| 5,780,534 A | 7/1998 | Kleiner et al. | |
| 6,013,707 A | 1/2000 | Kleiner et al. | |
| 6,090,968 A | 7/2000 | Horold et al. | |
| 6,214,812 B1 | 4/2001 | Karpeisky | |
| 6,278,012 B1 * | 8/2001 | Horold et al. | 558/110 |
| 6,303,674 B1 * | 10/2001 | Kleiner | 524/133 |
| 6,355,832 B1 | 3/2002 | Weferling et al. | |
| 6,384,022 B1 | 5/2002 | Jackson et al. | |
| 6,569,974 B1 | 5/2003 | Sicken et al. | |
| 6,727,335 B2 | 4/2004 | Sicken et al. | |
| 6,855,757 B2 | 2/2005 | Horold et al. | |
| 7,446,140 B2 | 11/2008 | Bauer | |
| 7,473,794 B2 | 1/2009 | Wehner et al. | |
| 7,485,745 B2 | 2/2009 | Maas et al. | |
| 7,749,985 B2 | 7/2010 | Gallop et al. | |
| 7,829,736 B2 | 11/2010 | Wehner et al. | |
| 8,084,518 B2 | 12/2011 | Bauer | |
| 8,097,753 B2 | 1/2012 | Maas et al. | |
| 2002/0187977 A1 | 12/2002 | Pearlman et al. | |
| 2003/0171466 A1 | 9/2003 | Horold et al. | |
| 2003/0216533 A1 | 11/2003 | Sicken et al. | |
| 2005/0187196 A1 | 8/2005 | Madrid et al. | |
| 2006/0084734 A1 | 4/2006 | Bauer et al. | |
| 2006/0194973 A1 | 8/2006 | Gainer et al. | |
| 2006/0264654 A1 | 11/2006 | Wehner | |
| 2007/0210288 A1 | 9/2007 | Maas et al. | |
| 2007/0213436 A1 | 9/2007 | Maas et al. | |
| 2007/0213563 A1 | 9/2007 | Maas et al. | |
| 2008/0183009 A1 | 7/2008 | Wehner et al. | |
| 2008/0214708 A1 | 9/2008 | Bauer et al. | |
| 2009/0286759 A1 | 11/2009 | Gallop et al. | |
| 2010/0093239 A1 | 4/2010 | Bauer et al. | |
| 2011/0201733 A1 | 8/2011 | Hill et al. | |
| 2011/0213052 A1 | 9/2011 | Hill et al. | |
| 2011/0213059 A1 | 9/2011 | Hill et al. | |
| 2011/0213060 A1 | 9/2011 | Hill et al. | |
| 2011/0213061 A1 | 9/2011 | Hill et al. | |
| 2011/0213062 A1 | 9/2011 | Hill et al. | |
| 2011/0213078 A1 | 9/2011 | Hill et al. | |
| 2011/0213079 A1 | 9/2011 | Hill et al. | |
| 2011/0213080 A1 | 9/2011 | Hill et al. | |
| 2011/0224339 A1 | 9/2011 | Hill et al. | |
| 2011/0224340 A1 | 9/2011 | Hill et al. | |
| 2011/0237720 A1 | 9/2011 | Hill et al. | |
| 2011/0237721 A1 | 9/2011 | Hill et al. | |
| 2011/0237722 A1 | 9/2011 | Hill et al. | |
| 2011/0245385 A1 | 10/2011 | Hill et al. | |
| 2011/0245386 A1 | 10/2011 | Hill et al. | |
| 2011/0251310 A1 | 10/2011 | Hill et al. | |
| 2011/0251314 A1 | 10/2011 | Hill et al. | |
| 2011/0275744 A1 | 11/2011 | Hill et al. | |
| 2011/0281983 A1 | 11/2011 | Hill et al. | |
| 2012/0064790 A1 | 3/2012 | Bauer et al. | |

FOREIGN PATENT DOCUMENTS

| | | |
|---|---|---|
| DE | 2236036 | 2/1974 |
| DE | 2236037 | 2/1974 |
| DE | 2302523 | 2/1974 |
| DE | 2344332 | 3/1975 |
| DE | 2441878 | 3/1976 |
| DE | 2623775 | 12/1976 |
| DE | 2942781 | 4/1980 |
| DE | 10153780 | 11/2002 |
| DE | 19912920 | 9/2009 |
| EP | 00858391 | 8/1983 |
| EP | 0319482 | 6/1989 |
| EP | 0463560 | 1/1992 |
| EP | 0699708 | 3/1996 |
| EP | 0906915 | 4/1999 |
| EP | 1203770 | 5/2002 |
| EP | 1369422 | 12/2003 |
| EP | 1607400 | 12/2005 |
| EP | 1693403 | 8/2006 |
| EP | 1832594 | 9/2007 |
| EP | 1832595 | 9/2007 |
| EP | 1832596 | 9/2007 |
| EP | 1905776 | 4/2008 |
| ER | 0969008 | 1/2000 |
| GB | 1045684 | 10/1966 |
| JP | 05230085 | 9/1993 |
| WO | WO 99/28327 | 6/1999 |
| WO | WO 01/42252 | 6/2001 |
| WO | WO 0157050 | 8/2001 |
| WO | WO 02/100871 | 12/2002 |
| WO | WO 2005/014604 | 2/2005 |
| WO | WO 2005/032494 | 4/2005 |
| WO | WO 2005/044830 | 5/2005 |
| WO | WO 2007/052169 | 5/2007 |
| WO | WO 2008/033572 | 3/2008 |
| WO | WO 2008/043499 | 4/2008 |

OTHER PUBLICATIONS

English Translation of the PCT International Preliminary Report on Patentability PCT/EP2009/007123 mailed May 19, 2011.

Montchamp; "Recent advances in phosphorus—carbon bond formation. synthesis of H-phosphinic acid derivatives from hypophosphus compounds" Journal of Organometallic Chemistry Elsevier-Sequoua S.A. Lausanne, CH, vol. 690; pp. 2388-2406; XP004877374 (May 16, 2005).

Sylvine Deprele et al. "Palladium-Catalyzed Hydrophosphinylation of Alkenes and Alkynes;" Journal of the American Chemical Society, American Chemical Society, Washington DC, US vol. 124, No. 32 p. 9387, XP002500862 (Jan. 1, 2002).

Bravo-Altamirano et al.: "A Novel Approach to Phosphinic Acids from Hypophosphorus Acid;" Tetrahedron Letters, Elsevier, Amsterdam, NL vol. 48, No. 33, pp. 5755-5759, XP022163552 (Jul. 19, 2007).

Sylvine Depreie et al.: "Environmentally Benign Synthesis of H-Phosphinic Acids Using a Water Tolerant, Recyclable Polymer-Supported Catalyst," Organic Letters, American Chemical Society, US, vol. 6, No. 21, pp. 3805-3808 XP002500861 (Jan. 1, 2004).

Patrice Ribiere et al: "NiCL2-Catalyzed Hydrophosphinylation;" Journal of Organic Chemistry, American Chemical Society, Easton, US, vol. 70, No. 10, pp. 4064-4072, XP002530191 (Jan. 1, 2005).

Courdray L. et al.: "Allylic Phosphinates via Pd-Catalyzed Allylation of H-Phosphinic Acids with Allylic Alcohols;" Organic letters, vol. 10, No. 6, pp. 1123-1126 XP002561368 (Feb. 21, 2008).

Mastalerz Synthesis of some ethyiene-(P,P'-Dialkyl)-Diphosphic Acids as new Potential Antimetabolites of Succinic Acid; Roczniki Chemii Ann. Soc. Chim. Polonorum, vol. 38 pp. 61-66 XP 009126234 (1964).

Kurdyumova et al.: "Synthesis of Phosphinic Acids from Hypophosphites I Acrylates as an Unsaturated Component;" Russian Journal of General Chemistry (Translation of Zhurnal Obshchei Khimii (1997), 67(12) pp. 1852-1856 (Apr. 25, 1997).

Houben-Weyl, vol. 1211 , pp. 258-259 (Apr. 22, 1963).

Houben-Weyl, vol. 1211 , p. 306 (Apr. 22, 1963).

English abstract of Khairullin et al, "Reaction of chlorides of acids of trivalent phosphorus with conjugated systems I. Reaction of ethylphosphonous dichloride with alpha-beta-unstaturated acids" Zh. Obshch. Khimii. 36, pp. 289-296 (1966).

PCT International search report for PCT/EP2009/007124, mailed Feb. 22, 2010.

PCT International Preliminary Report on Patentability for PCT/EP2009/007124, mailed May 19, 2011.

Piotr Makewski: "A New Method for the Preparation of Bis(1-hydroxyalkyl)-phosphinic Acids;" Synthesis, vol. 6, pp. 555-557, XP002558292 (1987).

Hung Kuei Lin et al.: "Competitive inhibition of interfacial catalysis by phospholipase A2: differential interaction of inhibitors with the

(56) References Cited

OTHER PUBLICATIONS vesicle interface a controlling factor of inhibitor potency" J. Am. Chem. Soc, vol. 115, No. 10, 1993, pp. 3932-3942 XP009126627 (1993).

Kallinowsky G. et al.: "C13 Nuclear Magnetic Resonance Study of Some Phosphinolipids: Assignments and Conformational Studies;" Magnetic Resonance in Chemistry, vol. 27, No. 7, pp. 647-652 XP002558647 (1989).

PCT International Search Report for PCT/EP2009/007125, mailed Feb. 22, 2010.

English translation of PCT International Preliminary Report on Patentability for PCT/EP2009/007125, mailed May 19, 2011.

PCT International search report for PCT/EP2009/007126, mailed Sep. 2, 2010.

English translation of PCT International Preliminary Report on Patentability for PCT/EP2009/007126, mailed May 19, 2011.

Froestl W. et al.; "Phosphinic Acid Analogues of Gaba. 2. Selective, Orally Acitve Gabab Antagonists," Journal of Medicinal Chemistry, American Chemical Society, Washington, US, vol. 38, No. 17, pp. 3313-3331, XP000999491 (Jan. 1, 1995).

PCT International Preliminary Report on Patentability for PCT/EP2009/007127, mailed Jan. 18, 2010.

English translation of PCT International Preliminary Report on Patentability for PCT/EP2009/007127, mailed May 19, 2011.

PCT International Preliminary Report on Patentability for PCT/EP2009/007128, mailed Jan. 27, 2010.

English translation of PCT International Preliminary Report on Patentability for PCT/EP2009/007128, mailed May 19, 2011.

PCT International Preliminary Report on Patentability for PCT/EP2009/007129, mailed Feb. 22, 2010.

English translation of PCT International Preliminary Report on Patentability for PCT/EP2009/007129, mailed May 19, 2011.

PCT International Preliminary Report on Patentability for PCT/EP2009/007130, mailed Apr. 29, 2010.

English translation of PCT International Preliminary Report on Patentability for PCT/EP2009/007130, mailed May 19, 2011.

Nifant'ev et al.: "Reactions of acetylenes with hypophosphorous aand phosphous acids;" Journal of General Chemistry USSR Consultants Bureau, New York, NY, US vol. 56 No. 4 pp. 680-688 XP002165520 (Sep. 20, 1986).

English Abstract for DE 2344332, Mar. 27, 1975.

Kabachnik et al.: "Synthesis and properties of some ethylenepiphosphoryl compounds," Russian Chemical Bulletin, vol. 23, No. 10 p. 2205 XP002557075 (1974).

Saratovskikh I. et al.: "Phosphorus-containing Aminocarboxylic Acids: XIV. Synthesis of Analogs of [alpha]-Substituted Glutamic Acid" Russian Journal of General Chemistry Nauka/Interperiodica, Mo. vol. 75, No. 7 pp. 1077-1084 XP019301159 (Jul. 1, 2005).

Chemical Abstracts Service, Columbus, Ohio, US: Gereev et al.: "Stereochemistry of a 1,3-dipolar cycloaddition of diazomethane to alpha-substituted vinylphosphoryl compounds containing a chiral phosphorus atom" XP002567581 (1979).

Chemical Abstracts Service, Columbus, Ohio, US: Raevskii et al. "Electron-donor and acceptor functions of physiologically active and model compounds. V. Calculation of the electron-donor function of phosphoryl oxygen" XP002567582 (1984).

Isabelle Abrunhosa Thomas et al.: "Alkylation of H-Phosphinate Esters under Basic Conditions;" Jounal of Organic Chemistry, American Chemical Society, Easton.; US, vol. 72, No. 8 pp. 2851-2856 XP002530192 (Jan. 1, 2007).

Catherine Ruffin et al.: "Tetrakis(trimethylsilyl)hypophosphate P2O2(OTMS)4: Synthesis, reactivity and application as flame retardants;" Heteroatom Chemistry, VCH publishers, Defield Beach, FL, US, vol. 18, No. 7 pp. 721-731 XP009118331 (Nov. 6, 2007).

PCT International Search Report for PCT/EP2009/007131, mailed Feb. 8, 2010.

English translation of the PCT International Preliminary Report on Patentability for PCT/EP2009/007131, mailed May 19, 2011.

PCT International Preliminary Report on Patentability for PCT/EP2009/007132, mailed Feb. 15, 2010.

English translation of PCT International Preliminary Report on Patentability for PCT/EP2009/007132, mailed May 19, 2011.

PCT International Preliminary Report on Patentability for PCT/EP2009/007133, mailed Feb. 3, 2010.

English translation of PCT International Preliminary Report on Patentability for PCT/EP2009/007133, mailed May 19, 2011.

Database Beilstein [Online] Beilstein Institute for Organic Chemistry; Frankfurt-Main, DE; XP002561148, retrived from xfire Database accession No. Reaction ID 198358. abstract (1954).

PCT International Preliminary Report on Patentability for PCT/EP2009/007134, mailed Feb. 18, 2010.

English translation of PCT International Preliminary Report on Patentability for PCT/EP2009/007134, mailed May 19, 2011.

PCT International Preliminary Report on Patentability for PCT/EP2009/007135, mailed Mar. 17, 2010.

English translation of PCT International Preliminary Report on Patentability for PCT/EP2009/007135, mailed May 26, 2011.

Bravo-Altamirano et al.: "Palladium Catalyzed Reaction of Hypophosphorous Compounds with Allenes, Dienes, and Allylic Electrophiles: Methodology for the Synthesis of Allylic H-Phosphinates" J. Org. Chem., vol. 73, No. 6, pp. 2292-2301 XP002567417 (Feb. 15, 2008).

Nadia Valiaeva et al.: "Phosophinic Acid Pseudopeptides Analogous to Glutamyl-gamma-glutamate: Synthesis and Coupling to Pteroyl Azides Leads to Potent Inhibitors of Folypoly-gamma-glutamate Synthetase;" J. Or. Chem., vol. 66, pp. 5146-5154 XP002567418 (2001).

Yamagishi takehiro et al.: "Stereoselective Synthesis of beta-Amino-alpha-hydroxy(allyl)phosphinates and an Application to the Synthesis of a Building Block for Phosphinyl Peptides" Synlett, No. 9, pp. 1471-1474, XP 002567142 (Jan. 1, 2002).

PCT International Search Report for PCT/EP2009/007136, mailed Mar. 22, 2010.

English translation of the PCT International Preliminary Report on Patentability for PCT/EP2009/007136, mailed Jun. 16, 2011.

Database Beilstein [online] Beilstein Institute for Organic Chemistry, Frankfurt-Main, DE; Database accession No. Reaction ID 101395 XP 002567148 (1956).

PCT International Search Report for PCT/EP2009/007137, mailed Mar. 12, 2010.

English translation of the PCT International Preliminary Report on Patentability for PCT/EP2009/007137, mailed Jun. 16, 2011.

Yamagishi et al.: "Diastereoselective synthesis of beta-substituted alpha-hydroxyphosphinates through hydrophosphinylation of alpha-heteroatom-substituted aldehydes;" Tetrahedron, Elsevier Science Publishers, Amsterdam, NL., vol. 59, No. 6 pp. 767-772 XP004404933 (Feb. 3, 2003).

Database Beilstein [online] Beilstein Institute for Organic Chemistry, Frankfurt-Main, DE; Database accession No. Reaction ID 970178 XP 002571550 (1963).

PCT International Search Report for PCT/EP2009/007139, mailed Mar. 22, 2010.

English translation of the PCT International Preliminary Report on Patentability for PCT/EP2009/007139, mailed Jun. 30, 2011.

PCT International Search Report for PCT/EP2009/007140, mailed Mar. 11, 2010.

English translation of the PCT International Preliminary Report on Patentability for PCT/EP2009/007140, mailed Jun. 30, 2011.

PCT International Search Report for PCT/EP2009/008964, mailed Jul. 9, 2010.

English translation of the PCT International Preliminary Report on Patentability for PCT/EP2009/008964, mailed Jun. 30, 2011.

Alonso et al.: "Transition-Metal Catalyzed Addition of Heteroatom-Hydrogen Bonds to Alkynes;" Chem. Rev., pp. 3148-3153 XP002556525 (2004).

Pudovick et al.: "Free Radical Reaction of Addition of Partial Esters of Phosphorus Acids to Acetylenic Hydrocarbons;" J. Gen. Chem. USSR, vol. 39, No. 5, pp. 985-988 XP009126232 (1969).

Database Beilstein [online] Beilstein Institute for Organic Chemistry, Frankfurt-Main, DE: Database accession No. Reaction BRN 3110535, retrieved from xfire XP002557076 (1967).

(56) References Cited

OTHER PUBLICATIONS

Database Beilstein [Online] Beilstein Institute for Organic Chemistry, Frankfurt-Main, DE; Database accession No. Reaction BRN 8075738 XP 002557077 (1997).
PCT International Search Report for PCT/EP2009/007142, mailed Feb. 9, 2010.
English translation of PCT International Preliminary Report on Patentability for PCT/EP2009/007142, mailed Jun. 30, 2011.
English Abstract for SU 314758, Sep. 21, 1971.
Sasse K ED-Sasse K: "Houben-Weyl Methoden der Organischen Chemie", Organische, Phosphor-Verbindungen; [Methoden der Organischen Chemie], Stuttgart, G. Thieme Verlag DE, XP002500739, pp. 257-259, 261, 294-301 (Jan. 1, 1963).
"1" In: Sasse K Ed-Sasse K: "Houben-Weyl Methoden der Organischen Chemie;" Organische Phosphor-Verbindungen; [Methoden der Organischen Chemie], Stuttgart, G. Thieme Verlag, DE, p. 358, XP002564325 (Jan. 1, 1963).
Regitz:"Houben-Weyl Methoden der Organischen Chemie" Organische Phosphor-Verbindungen; [Methoden der Organischen Chemie], Stuttgart, G. Thieme Verlag, DE, pp. 308-309 XP002564334 (Jan. 1, 1982).
Yamagishi et al.: "Lipase-catalyzed kinetic resolution of alpha-hydroxy-H-phosphinates" Tetrahedron Letters. Elsevier, Amsterdam, NL, vol. 45, No. 36, pp. 6713-6716 XP004556626 (Aug. 30, 2004).
Anderson et al.: "Antidiabetic agents: a new class of reversible carnitine palmitoyltrasferase I inhibitors;" J. Med. Chem., vol. 38, No. 18, pp. 3448-3450 XP002564326 (1995).
Karanewsky et al.: "Synthesis of Phosphinic Monoesters from Phosphonous Acids" Tetrahedron Letters, Elsevier, Amsterdam, NL, vol. 27, No. 16, pp. 1751-1754 XP001084930 (Jan. 1, 1986).
Issleib, et al.: "Synthese und Reaktionsverhalten der Athylen-bis-organophosphine;" Chemische Berichte, vol. 101, pp. 2197-2202 XP009126251.
PCT International Search Report for PCT/EP2009/007143, mailed Feb. 17, 2010.
English translation of the PCT International Preliminary Report on Patentability for PCT/EP2009/007143, mailed Jun. 30, 2011.
Regitz: "Houben-Weyl Methoden der Organishcen Chemie" p. 188, (Jan. 1, 1982).
Rezanka et al.: "Synthesis of a Bifunctional Monophosphinate DOTA Derivative Having a Free Carboxylate Group in the Phosphorus Side Chain;" Synthesis, Georg Thieme Verlag, Stuttgart pp. 1431-1435 XP009126087 (Sep. 1, 2008).
Database Beilstein [online] Beilstein Institute for Organic Chemistry, Frankfurt-Main, DE; Database accession No. Reaction ID 938840 XP002557780 (1962).
Diel et al.: "Organische Phosphorverbindungen 84. Herstellung Eigenschaften und Biologische Wirkung von Hydrazino-Methyl-Phosphon- und Phosphinsaeuren und Derivatin;" Phosphorus and Sulfur and the Related Elements, Gordon and Breach—Harwood Academic, CH, vol. 36, pp. 85-98 XP001105809 (Jan. 1, 1998).
Sasse K ED-Sasse K: "Houben-Weyl Methoden der Organischen Chemie", Organische Phosphor-Verbindungen; [Methoden der Organischen Chemie], Stuttgart, G. Thieme Verlag DE, XP002557781, pp. 228-229 (Jan. 1, 1963).
Kielbasinski et al: "Enzymatic reactions in ionic liquids: lipase-catalysed kinetic resolution of racemic, P-chiral hydroxymethanephosphinates and hydroxmethylphosphine oxides;" Tetrahedron Asymmetry, Pergamon Press Ltd, Oxford, GB, vol. 13, No. 7, pp. 735-738 XP004354866 (May 2, 2002).
Maier: "Organic Phosphorus compounds 91.1 Synthesis and Properties of 1-Amino-2-Arylethylphosphinic and -Phosphinic Acids as well as Phosphine Oxides;" Phosphorus, Sulfur and Silicon and the Related Elements, Gordon and Breach Science Publishers, Amsterdam, GB, vol. 53, No. 1/04 pp. 43-67 XP000671624 (Jan. 1, 1990).
English Translation of Houben-Weyl, vol. 1211, pp. 258-259 (Apr. 22, 1963).
English Translation of Houben-Weyl, vol. 1211, p. 306 (Apr. 22, 1963).
English Translation of Sasse K ED-Sasse K: "Houben-Weyl Methoden der Organischen Chemie", Organische Phosphor-Verbindungen; [Methoden der Organischen Chemie], Stuttgart, G. Thieme Verlag DE, XP002500739, pp. 257-259, 261, 294-301 (Jan. 1, 1963).
English Translation of "1" In: Sasse K Ed-Sasse K: "Houben-Weyl Methoden der Organischen Chemie;" Organische Phosphor-Verbindungen; [Methoden der Organischen Chemie], Stuttgart, G. Thieme Verlag, DE, p. 358, XP002564325 (Jan. 1, 1963).
English Translation of Regitz:"Houben-Weyl Methoden der Organischen Chemie" Organische Phosphor-Verbindungen; [Methoden der Organischen Chemie], Stuggart, G. Thieme Verlag, DE, pp. 308-309 XP002564334 (Jan. 1, 1982).
English Translation of Issleib, et al.: "Synthese und Reaktionsverhalten der Athylen-bis-organophosphine;" Chemische Berichte, vol. 101, pp. 2197-2202 XP009126251 (1968).
English Translation of Regitz: "Houben-Weyl Methoden der Organishcen Chemie" p. 188, (Jan. 1, 1982).
English Translation of Diel et al.: "Organische Phosphorverbindungen 84. Herstellung Eigenschaften und Biologische Wirkung von Hydrazino-Methyl-Phosphon- und Phosphinsaeuren und Derivatin;" Phosphorus and Sulfur and the Related Elements, Gordon and Breach—Harwood Academic, CH, vol. 36, pp. 85-98 XP001105809 (Jan. 1, 1998).
English Translation of Sasse K ED-Sasse K: "Houben-Weyl Methoden der Organischen Chemie", Organische Phosphor-Verbindungen; [Methoden der Organischen Chemie], Stuttgart, G. Thieme Verlag DE, XP002557781, pp. 228-229 (Jan. 1, 1963).
US 6,248,921, 06/2001, Weferling et al. (withdrawn)

* cited by examiner

METHOD FOR THE PRODUCTION OF MONOFUNCTIONALIZED DIALKYLPHOSPHINIC ACIDS, ESTERS AND SALTS, AND USE THEREOF

This invention relates to a method for producing monofunctionalized dialkylphosphinic acids, esters and salts and also to their use.

Monofunctionalized dialkylphosphinic acids are obtainable according to the prior art by addition of unsaturated compounds onto phenylphosphonous acid derivatives or methylphosphonous acid derivatives. The addition of alkenyl acetates onto the latter is known.

Phenylphosphonous acid derivatives and methylphosphonous acid derivatives have hitherto only been obtainable through use of phosphorus halogen compounds (phosphoryl trichloride), since the direct addition of a double-bonded reactant (olefin, aldehyde, ketone, etc) does not lead to these representatives.

The stagewise addition of olefins onto hypophosphorous acid or its salts or derivatives to form asymmetric dialkyl acids is not very well known and not preferred, since the free-radical addition of alkyl- or arylphosphinic esters onto nonactivated alpha-olefins gives moderate yields and unwanted telomeric by-products. Moreover, the addition reaction is nonselectively stepwise, instead leading to the twofold addition of the same olefin and appreciable by-product fractions in the form of symmetrical dialkylphosphinic acids.

Non-free-radically prepared functional derivatives of ethylphosphinic acid and amine-functionalized derivatives of ethylphosphinic acid are not known.

It is an object of the present invention to provide a halogen-free method for production of monofunctionalized dialkylphosphinic acids, esters and salts.

We have found that this object is achieved by a method for producing monofunctionalized dialkylphosphinic acids, esters and salts, which comprises a) reacting a phosphinic acid source (I)

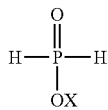

with olefins (IV)

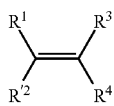

in the presence of a catalyst A to form an alkylphosphonous acid, salt or ester (II)

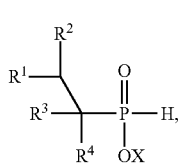

b) reacting the resulting alkylphosphonous acid, salt or ester (II) with compounds comprising C=C, C=O or C=N double bonds to form compounds (III) of the type

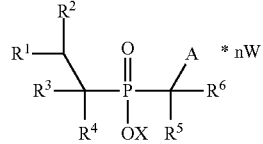

where $R^1$, $R^2$, $R^3$, $R^4$, $R^5$, $R^6$ are identical or different and are each independently H, $C_1$-$C_{18}$-alkyl, $C_6$-$C_{18}$-aryl, $C_6$-$C_{18}$-aralkyl, $C_6$-$C_{18}$-alkylaryl, CN, CHO, $OC(O)CH_2CN$, $CH(OH)C_2H_5$, $CH_2CH(OH)CH_3$, 9-anthracene, 2-pyrrolidone, $(CH_2)_mOH$, $(CH_2)_mNH_2$, $(CH_2)_mNCS$, $(CH_2)_mNC(S)NH_2$, $(CH_2)_mSH$, $(CH_2)_m$S-2-thiazoline, $(CH_2)_mSiMe_3$, $CHR^7(CH_2)_mCH_3$, $C(O)R^7$, $(CH_2)_mC(O)R^7$, $CH=CHR^7$, $R^5R^6C=CHR^7$ and/or $CH=CH-C(O)R^7$ and where $R^7$ is H, $C_1$-$C_8$-alkyl or $C_6$-$C_{18}$-aryl and m is an integer from 0 to 10 and X is H, $C_1$-$C_{18}$-alkyl, $C_6$-$C_{18}$-aryl, $C_6$-$C_{18}$-aralkyl, $C_6$-$C_{18}$-alkylaryl, $(CH_2)_kOH$, $CH_2$—CHOH—$CH_2OH$, $(CH_2)_kO(CH_2)_kH$, $(CH_2)_k$—CH(OH)—$(CH_2)_kH$, $(CH_2$—$CH_2O)_kH$, $(CH_2$—$C[CH_3]HO)_kH$, $(CH_2$—$C[CH_3]HO)_k(CH_2$—$CH_2O)_kH$, $(CH_2$—$CH_2O)_k$-alkyl, $(CH_2$—$C[CH_3]HO)_k$-alkyl, $(CH_2$—$C[CH_3]HO)_k(CH_2$—$CH_2O)_k$-alkyl, $(CH_2$—$CH_2O)_k(CH_2$—$C[CH_3]HO)$O-alkyl, $(CH_2)_k$—CH=$CH(CH_2)_kH$, $(CH_2)_kNH_2$ and/or $(CH_2)_kN[(CH_2)_kH]_2$, where k is an integer from 0 to 10, and/or Mg, Ca, Al, Sb, Sn, Ge, Ti, Fe, Zr, Zn, Ce, Bi, Sr, Mn, Cu, Ni, Li, Na, K, H and/or a protonated nitrogen base and where A is OH, $NH_2$, NHR, $NR^2$ or O—CO—$R^8$ and $R^8$ has the same meanings as $R^1$ to $R^6$ and W represents an inorganic acid, carboxylic acid, Lewis acid or organic acid, where n represents an integer or fraction ranging from 0 to 4 and the catalyst A comprises transition metals and/or transition metal compounds and/or catalyst systems composed of a transition metal and/or transition metal compound and at least one ligand.

Preferably, step b) comprises reacting the resulting alkylphosphonous acid, its salt or ester (II) first with compounds comprising C=C, C=O or C=N double bonds and then with $NHR_2$, $NH_2R$, $NH_3$ or salts thereof.

Alternatively, step b) comprises reacting the resulting alkylphosphonous acid, its salt or ester (II) simultaneously with compounds comprising C=C, C=O or C=N double bonds and with $NHR_2$, $NH_2R$, $NH_3$ or salts thereof.

Preferably, compounds of the formula (III) where A is O—CO—$R^8$ have the $R^8CO_2Y$ moiety detached from them in the presence of a catalyst B.

Preferably, the monofunctionalized dialkylphosphinic acid, its salt or ester (III) obtained after step b) is subsequently reacted in a step c) with metal compounds of Mg, Ca, Al, Sb, Sn, Ge, Ti, Fe, Zr, Zn, Ce, Bi, Sr, Mn, Li, Na, K and/or a protonated nitrogen base to form the corresponding monofunctionalized dialkylphosphinic acid salts (III) of these metals and/or of a nitrogen compound.

Preferably, the alkylphosphonous acid, salt or ester (II) obtained after step a) and/or the monofunctionalized dialkylphosphinic acid, salt or ester (III) obtained after step b) and/or the particular resulting reaction solution thereof are esterified with an alkylene oxide or an alcohol M-OH and/or M'-OH, and the respectively resulting alkylphosphonous ester (II) and/or monofunctionalized dialkylphosphinic ester (III) are subjected to the further reaction steps b) or c).

Preferably, the groups $C_6$-$C_{18}$-aryl, $C_6$-$C_{18}$-aralkyl and $C_6$-$C_{18}$-alkylaryl are substituted with $SO_3X_2$, $C(O)CH_3$, OH, $CH_2OH$, $CH_3SO_3X_2$, $PO_3X_2$, $NH_2$, $NO_2$, $OCH_3$, SH and/or $OC(O)CH_3$.

Preferably, $R^1$, $R^2$, $R^3$, $R^4$, $R^5$, $R^6$, $R^8$ are identical or different and are each independently H, methyl, ethyl, n-propyl, isopropyl, n-butyl, isobutyl, tert-butyl and/or phenyl.

Preferably, X is H, Ca, Mg, Al, Zn, Ti, Fe, Ce, methyl, ethyl, n-propyl, isopropyl, n-butyl, isobutyl, tert-butyl, phenyl, ethylene glycol, propyl glycol, butyl glycol, pentyl glycol, hexyl glycol, allyl and/or glycerol.

Preferably, the transition metals and/or transition metal compounds comprise such from the seventh and eighth transition groups.

Preferably, the transition metals and/or transition metal compounds comprise rhodium, nickel, palladium, platinum, and/or ruthenium.

Preferably, W is hydrochloric acid, sulfuric acid, nitric acid, phosphoric acid, phosphonic acid, phosphinic acid, formic acid, citric acid, propionic acid, butyric acid, lactic acid, palmitic acid, stearic acid, malonic acid, maleic acid, fumaric acid, tartaric acid, citric acid, ascorbic acid, trimethylborane, triethylborane, tributylborane or triphenylborane.

Preferably, the alcohol of the general formula M-OH comprises linear or branched, saturated and unsaturated, monohydric organic alcohols having a carbon chain length of $C_1$-$C_{18}$ and the alcohol of the general formula M'-OH comprises linear or branched, saturated and unsaturated polyhydric organic alcohols having a carbon chain length of $C_1$-$C_{18}$.

Preferably, the catalyst B comprises metals, metal hydrides, metal hydroxides and/or metal alkoxides.

Preferably, the catalyst B comprises lithium, lithium hydride, lithium aluminohydride, methyllithium, butyllithium, tertbutyllithium, lithium diisopropylamide, sodium, sodium hydride, sodium borohydride, sodium hydroxide, sodium methoxide, sodium ethoxide or sodium butoxide, potassium hydroxide, potassium methoxide, potassium ethoxide or potassium butoxide.

The present invention also provides for the use of monofunctionalized dialkylphosphinic acids, esters and salts obtained according to one or more of claims 1 to 12 as an intermediate for further syntheses, as a binder, as a crosslinker or accelerant to cure epoxy resins, polyurethanes and unsaturated polyester resins, as polymer stabilizers, as crop protection agents, as a therapeutic or additive in therapeutics for humans and animals, as a sequestrant, as a mineral oil additive, as a corrosion control agent, in washing and cleaning applications, in electronic applications, as a polymerization catalyst for polyesters, as a copolycondensable flame retardant for polyester and polyamide fibers, as a polyester masterbatch, as a heat and light stabilizer for polymers, as intermediates for angiotensin-converting enzyme inhibitors, as alanylaminopeptidase inhibitors for cell functional control and treatment of immunological, inflammatory, neuronal or other disorders or as an intermediate in the manufacture thereof, as a dipeptidylpeptidase IV inhibitor or as an intermediate in the manufacture thereof, as inhibitors of epoxide hydrolase for treatment of high blood pressure or as an intermediate in the manufacture thereof, for fiber pretreatment and fiber surface modification.

The present invention also provides for the use of monofunctionalized dialkylphosphinic acids, salts and esters obtained according to one or more of claims 1 to 12 as a flame retardant, more particularly as a flame retardant for clearcoats and intumescent coatings, as a flame retardant for wood and other cellulosic products, as a reactive and/or nonreactive flame retardant for polymers, in the manufacture of flame-retardant polymeric molding materials, in the manufacture of flame-retardant polymeric molded articles and/or for flame-retardant finishing of polyester and cellulose straight and blend fabrics by impregnation.

The present invention also includes flame-retardant thermoplastic or thermoset polymeric molding material containing 0.5% to 45% by weight of monofunctionalized dialkylphosphinic acids, salts or esters obtained according to one or more of claims 1 to 15, 0.5% to 99% by weight of thermoplastic or thermoset polymer or mixtures thereof, 0% to 55% by weight of additives and 0% to 55% by weight of filler or reinforcing materials, wherein the sum total of the components is 100% by weight.

Lastly, the invention provides more flame-retardant thermoplastic or thermoset polymeric molded articles, films, threads and fibers containing 0.5% to 45% by weight of monofunctionalized dialkylphosphinic acids, salts or esters obtained according to one or more of claims 1 to 15, 0.5% to 99% by weight of thermoplastic or thermoset polymer or mixtures thereof, 0% to 55% by weight of additives and 0% to 55% by weight of filler or reinforcing materials, wherein the sum total of the components is 100% by weight.

Preferably m=1 to 10 and k=2 to 10. Preferably n represents 0, ¼, ⅓, ½, 1 2, 3 and 4.

All the reactions can also be carried out in stages; similarly, the various processing steps can also utilize the respective resulting reaction solutions.

Preferred compounds having C=X double bonds are those having C=O double bonds, preference here being given to ketones of the type $R^5R^6C$=O or aldehydes of the type $R^5CHO$.

Suitable aldehydes are for example acetaldehyde, benzylglyceraldehyde, butyraldehyde, decanal, formaldehyde, glutaraldehyde, glyoxal, glyoxylic acid, glyoxylic acid monohydrate, hexanal, isobutyraldehyde, lauraldehyde, 3-methylbutyraldehyde, octanal, enanthaldehyde, paraformaldehyde, pelargonaldehyde, 2-phenylpropionaldehyde, 3-phenylpropionaldehyde, propionaldehyde, 2,5,7,7-tetramethyloctanal, undecanal, valeraldehyde, citral, citronellal, crotonaldehyde, trans-2-hexenal, alpha-methylcinnamaldehyde, trans-2-pentenal, cinnamaldehyde, 4-acetoxy-3-methoxybenzaldehyde, 2-benzyloxybenzaldehyde, 2,4-dihydroxybenzaldehyde, 2,3-dihydroxybenzaldehyde, 2,5-dimethoxybenzaldehyde, ethylvaniline, 2-hydroxy-3-methoxybenzaldehyde, 2-hydroxy-4-methoxybenzaldehyde, 2-hydroxy-5-methoxybenzaldehyde, 2-hydroxy-6-methoxybenzaldehyde, 3-hydroxy-4-methoxybenzaldehyde, salicylaldehyde, benzaldehyde, 4-acetamidobenzaldehyde, 4-acetoxybenzaldehyde, anthracene-9-carbaldehyde, biphenyl-4-carbaldehyde, 4-dimethylaminobenzaldehyde, 2,4-dimethylbenzaldehyde, 3,5-dimethylbenzaldehyde, isophthalaldehyde, 4-isopropylbenzaldehyde, 2-methylbenzaldehyde, 3-methylbenzaldehyde, 4-methylbenzaldehyde, naphthalene-1-carbaldehyde, naphthalene-2-carbaldehyde, phthalaldehydic acid, phthalaldehyde, terephthalaldehydic acid, terephthalaldehyde, 2,4,6-trimethylbenzaldehyde, furfural, indol-3-carbaldehyde, 1-methylpyrrol-2-carbaldehyde, pyridine-2-carbaldehyde, pyridine-3-carbaldehyde, pyridin-4-carbaldehyde, pyrrol-2-carbaldehyde.

Preferred ketones are acetone, diisobutyl ketone, methyl n-propyl ketone; methyl ethyl ketone, methyl i-butyl ketone.

Preferred aldehydes are acetaldehyde, formaldehyde, paraformaldehyde, propionaldehyde, benzaldehyde.

In an alternative process design, the reaction in step a) is followed by a step b) comprising reacting compound (II) with compounds comprising C=X double bonds in the presence of a catalyst B to first form compounds of the formula (III)

where A in the formula (III) has the exclusive meaning of O—CO—R$^8$ and then detaching the R$^8$CO$_2$Y moiety.

The detachment of R$^8$CO$_2$Y from the monofunctionalized dialkylphosphinic acid, its salts and esters (III) is achieved by acidic or alkaline hydrolysis using acids or bases in the presence of water, wherein Y represents H, Mg, Ca, Al, Sb, Sn, Ge, Ti, Fe, Zr, Zn, Ce, Bi, Sr, Mn, Cu, Ni, Li, Na, K, H and/or a protonated nitrogen base.

In the event that the compounds having C=X double bonds are those having C=C double bonds, those of the type R$^9$R$^{10}$C=C(R$^5$)—O—CO(R$^8$), where R$^9$ and R$^{10}$ are identical or different and each is independently H, C$_1$-C$_{18}$-alkyl, C$_6$-C$_{18}$-aryl, C$_6$-C$_{18}$-aralkyl, C$_6$-C$_{18}$-alkylaryl, CN, CHO, OC(O)CH$_2$CN, CH(OH)C$_2$H$_5$, CH$_2$CH(OH)CH$_3$, 9-anthracene, 2-pyrrolidone, (CH$_2$)$_m$OH, (CH$_2$)$_m$NH$_2$, (CH$_2$)$_m$NCS, (CH$_2$)$_m$NC(S)NH$_2$, (CH$_2$)$_m$SH, (CH$_2$)$_m$S-2-thiazoline, (CH$_2$)$_m$SiMe$_3$, CHR$^7$(CH$_2$)$_m$CH$_3$, C(O)R$^7$, (CH$_2$)$_m$C(O)R$^7$, CH=CHR$^7$ and/or CH=CH—C(O)R$^7$, and R$^7$ represents H, C$_1$-C$_8$-alkyl or C$_6$-C$_{18}$-aryl and m is an integer from 0 to 10, are preferred.

Preferred compounds having C=C double bonds are vinyl acetate, vinyl propionate, vinyl butyrate, vinyl pivalate, vinyl benzoate, vinyl cinnamate, vinyl stearate, vinyl laurate, 1-propenyl acetate, 1-propenyl propionate, 1-propenyl butyrate, 1-propenyl pivalate, 1-propenyl benzoate, 1-propenyl cinnamate, 1-propenyl stearate, 1-propenyl laurate, 1-butenyl acetate, 1-butenyl propionate, 1-butenyl butyrate, 1-butenyl pivalate, 1-butenyl benzoate, 1-butenyl cinnamate, 1-butenyl stearate, 1-butenyl laurate.

Preference is given to using the catalyst B in amounts of 0.05 to 110 mol % based on the particular compounds having C=C double bonds.

Preference is given to using the catalyst B in amounts of 0.001 to 110 mol %, based on the phosphorus-containing compound (II).

Suitable solvents are those used in process stage a).

The catalyst B is preferably metered at a rate of 0.01 to 110 mol % of catalyst per hour, based on the phosphorus-containing compound (II).

The temperature for the reaction of the alkylphosphonous acids (II) with compounds having C=C double bonds is preferably in the range from 0 to 250° C., more preferably in the range from 20 to 200° C. and more particularly in the range from 50 to 150° C.

The atmosphere for the reaction with compounds having C=C double bonds preferably consists of constituents of the solvent and compounds having C=C double bonds to an extent in the range from 50% to 99.9% by weight and preferably 70-95%.

When a monofunctionalized dialkylphosphinic acid salt (III) is obtained, it can be reacted with a mineral acid to form the corresponding acid and be esterified with an alcohol M-OH or M'-OH or an alkylene oxide.

When a monofunctionalized dialkylphosphinic acid (III) is obtained, it can be reacted with a base to form a monofunctionalized dialkylphosphinic acid salt.

Suitable mineral acids are for example hydrochloric acid, sulfuric acid, nitric acid or phosphoric acid or mixtures thereof.

The acidic or alkaline hydrolysis may preferably be carried out in the presence of water and an inert solvent. Suitable inert solvents are the solvents mentioned in process step a), preference being given to low molecular weight alcohols having 1 to 6 carbon atoms. The use of saturated aliphatic alcohols is particularly preferred. Examples of suitable alcohols are methanol, ethanol, propanol, i-propanol, butanol, 2-methyl-1-propanol, n-pentanol, 2-pentanol, 3-pentanol, 2-methyl-2-butanol, 3-methyl-2-butanol, 2-methyl-3-butanol, 3-methyl-1-butanol or 2-methyl-1-butanol.

Preferred bases for carrying out the alkaline hydrolysis are metals, metal hydrides and metal alkoxides such as for example lithium, lithium hydride, lithium aluminohydride, methyllithium, butyllithium, t-butyllithium, lithium diisopropylamide, sodium, sodium hydride, sodium borohydride, sodium methoxide, sodium ethoxide or sodium butoxide, potassium methoxide, potassium ethoxide or potassium butoxide and also sodium hydroxide, potassium hydroxide, lithium hydroxide, barium hydroxide and ammonium hydroxide. Preference is given to using sodium hydroxide, potassium hydroxide and barium hydroxide.

Preferred mineral acids for carrying out the acidic hydrolysis are for example sulfuric acid, nitric acid, hydrochloric acid, phosphoric acid or mixtures thereof. Preference is given to using sulfuric acid or hydrochloric acid.

The presence of water is essential to carrying out the hydrolysis. The amount of water can range from the stoichiometric requirement as minimum level to an excess.

The hydrolysis is preferably carried out in a phosphorus/water molar ratio of 1:1 to 1:1000 and more preferably in the range from 1:1 to 1:10.

The hydrolysis is preferably carried out in a phosphorus/base or acid molar ratio of 1:1 to 1:300 and more preferably in the range from 1.1 to 1:20.

The amount of alcohol used is generally in the range from 0.5 kg to 1.5 kg per kg of the monofunctionalized dialkylphosphinic acid, salts or esters (III), preferably in the range from 0.6 kg to 1.0 kg.

The reaction temperature is in the range from 50° C. to 140° C. and preferably in the range from 80° C. to 130° C.

The reaction is preferably carried out at a total pressure in the range from 1 to 100 bar and more preferably at a total pressure in the range from 1 to 10 bar.

The reaction time is preferably in the range from 0.2 to 20 hours and more preferably in the range from 1 to 13 hours.

In a further process variant, step b) comprises reacting compounds (II) with compounds comprising C=X double bonds and simultaneously or in succession with NHR$_2$, NH$_2$R, NH$_3$ or their salts.

Suitable salts derive from the reaction of NHR$_2$, NH$_2$R, NH$_3$ with hydrochloric acid, sulfuric acid, nitric acid or phosphoric acid, phosphonic acid, phosphinic acid, formic acid, acetic acid, propionic acid, butyric acid, lactic acid, palmitic acid, stearic acid, malonic acid, maleic acid, fumaric acid, tartaric acid, citric acid, ascorbic acid, trimethylborane, triethylborane, tributylborane or triphenylborane.

Preferred representatives of NH$_2$R are NH$_2$Et, H$_2$NCH(C$_6$H$_5$)$_2$ or their salts.

The R group is preferably detached from the monofunctionalized dialkylphosphinic acids, esters or salts (III) by reaction with mineral acids or by reaction with hydrogen in the presence of a catalyst C.

Preferred mineral acids for detaching the R group are the mineral acids mentioned above.

The preferred catalytic detachment of R is effected by means of hydrogen in the presence of a catalyst C and in the presence or absence of a promoter.

The catalyst C as for process step b) for the reaction of the monofunctionalized dialkylphosphinic acid derivative (III) with hydrogen in the presence or absence of a promoter to form the monofunctionalized dialkylphosphinic acid derivatives (III) may preferably be the catalyst A.

In addition to the ligands listed under catalyst A, the following compounds can also be used:

diphenyl p-, m- or o-tolyl phosphite, di-p-, -m- or -o-tolyl phenyl phosphite, m-tolyl o-tolyl p-tolyl phosphite, o-tolyl p- or m-tolyl phenyl phosphite, di-p-tolyl m- or o-tolyl phosphite, di-m-tolyl p- or o-tolyl phosphite, tri-m-, -p- or -o-tolyl phosphite, di-o-tolyl m- or p-tolyl phosphite; tris(2-ethylhexyl)phosphite, tribenzyl phosphite, trilauryl phosphite, tri-n-butyl phosphite, triethyl phosphite, tri-neopentyl phosphite, tri-i-propyl phosphite, tris(2,4-di-t-butylphenyl) phosphite, tris(2,4-di-tert-butylphenyl)phosphite, diethyl trimethylsilyl phosphite, diisodecyl phenyl phosphite, dimethyl trimethylsilyl phosphite, triisodecyl phosphite, tris(tert-butyldimethylsilyl) phosphite, tris(2-chloroethyl phosphite, tris(1,1,1,3,3,3-hexafluoro-2-propyl)phosphite, tris(nonylphenyl)phosphite, tris(2,2,2-trifluoroethyl)phosphite, tris(trimethylsilyl)phosphite, 2,2-dimethyltrimethylene phenyl phosphite, trioctadecyl phosphite, triimethylolpropane phosphite, benzyldiethyl phosphite, (R)-binaphthyl isobutyl phosphite, (R)-binaphthyl cyclopentyl phosphite, (R)-binaphthyl isopropyl phosphite, tris(2-tolyl)phosphite, tris(nonylphenyl)phosphite, methyl diphenyl phosphite; (11aR)-(+)-10,11,12,13-tetrahydrodiindeno[7,1-de:1',7'-fg][1,3,2]dioxaaphosphocine-5-phenoxy, 4-ethyl-2,6,7-trioxa-1-phosphabicyclo[2.2.2]octane, (11bR,11bR)-4,4'-(9,9-dimethyl-9H-xanthene-4,5-diyl)bisdinaphtho[2,1-d:1',2'-f][1,3,2]dioxaphosphepine, (11bR, 11'bR)-4,4'-(oxydi-2,1-phenylene)bisdinaphtho[2,1-d: 1',2'-f][1,3,2]dioxaphosphepine, (11bS,11'bS)-4,4'-(9,9-dimethyl-9H-xanthene-4,5-diyl)bisdinaphtho[2,1-d:1',2'-f][1,3,2]dioxaphosphepine, (11bS,11'bS)-4,4'-(oxydi-2,1-phenylene)bisdinaphtho[2,1-d: 1',2'f][1,3,2]dioxaphosphepine, 1,1'-bis[(11bR)- and 1,1'-bis[(11bS)-dinaphtho[2,1-d:1',2'-f][1,3,2]dioxaphosphepine-4-yl]ferrocene; dimethyl phenylphosphonite, diethyl methylphosphonite, diethyl phenylphosphonite, diisopropyl phenylphosphonite; methyl methylphenylphosphinite, isopropyl isopropylphenylphosphinite, ethyl diphenylphosphinite and methyl diphenylphosphinite.

In addition to the bidentate ligands listed under catalyst A, the following compounds can also be used:

1,2-bis(diadamantylphosphinomethyl)benzene, 1,2-bis(di-3,5-dimethyladamantyl-phosphinomethyl)benzene, 1,2-bis(di-5-tert-butyladamantaylphosphino-methyl)benzene, 1,2-bis(1-adamantyl tert-butylphosphinomethyl)benzene, 1-(di-tert-butylphosphinomethyl)benzene, 1-(diadamantylphosphinomethyl)-2-(phosphaadamantylphosphinomethyl)benzene, 1,2-bis(di-tert-butylphosphino-methyl)ferrocene, 1,2-bis(dicyclohexylphosphinomethyl)ferrocene, 1,2-bis(di-isobutylphosphinomethyl)ferrocene, 1,2-bis(dicyclopentylphosphino-methyl)ferrocene, 1,2-bis(diethylphosphinomethyl)ferrocene, 1,2-bis(diisopropyl-phosphinomethyl)ferrocene, 1,2-bis(dimethylphosphinomethyl)ferrocene, 9,9-dimethyl-4,5-bis(diphenoxyphosphine)xanthene, 9,9-dimethyl-4,5-bis(di-p-methylphenoxyphosphine)xanthene, 9,9-dimethyl-4,5-bis(di-o-methylphenoxy-phosphine)xanthene, 9,9-dimethyl-4,5-bis(di-1,3,5-trimethylphenoxyphosphine)xanthene, 9,9-dimethyl-4,5-bis(diphenoxyphosphine)-2,7-di-tert-butylxanthene, 9,9-dimethyl-4,5-bis(di-o-methylphenoxyphosphine)-2,7-di-tert-butylxanthene, 9,9-dimethyl-4,5-bis(di-p-methylphenoxyphosphine)-2,7-di-tert-butylxanthene, 9,9-dimethyl-4,5-bis(di-1,3,5-trimethylphenoxyphosphine)-2,7-di-tert-butylxanthene, 1,1'-bis(diphenoxyphosphine)ferrocene, 1,1'-bis(di-o-methylphenoxy)ferrocene, 1,1'-bis(di-p-methylphenoxyphosphine)ferrocene, 1,1-bis(di-1,3,5-trimethylphenoxyphosphine)ferrocene, 2,2'-bis(diphenoxyphosphine)-1,1'-binaphthyl, 2,2'-bis(di-o-methylphenoxyphosphine)-1,1'-binaphthyl, 2,2'-bis(di-p-methylphenoxyphosphine)-1,1'-binaphthyl, 2,2'-bis(di-1,3,5-trimethylphenoxyphosphine)-1,1'-binaphthyl, (oxydi-2,1-phenylene)bis(diphenoxyphosphine), (oxydi-2,1-phenylene)bis(di-o-methylphenoxyphosphine), (oxydi-2,1-phenylene)bis(di-p-methylphenoxyphosphine), (oxydi-2,1-phenylene)bis(di-1,3,5-trimethylphenoxyphosphine), 2,2'-bis(diphenoxyphosphine)-1,1'-biphenyl, 2,2'-bis(di-o-methylphenoxyphosphine)-1,1'-biphenyl, 2,2'-bis(di-p-methylphenoxyphosphine)-1,1'-biphenyl, 2,2'-bis(di-1,3,5-trimethylphenoxyphosphine)-1,1'-biphenyl, 1,2-bis(di-(1,3,5,7-tetramethyl-6,9,10-trioxa-2-phosphaadamantylmethyl)ferrocene, 1-(tert-butoxycarbonyl)-(2S,4S)-2-[(diphenylphosphino)methyl]-4-(dibenzophospholyl)pyrrolidine, 1-(tert-butoxycarbonyl)-(2S,4S)-2-[(dibenzophospholyl)methyl]-4-(diphenylphosphino)pyrrolidine, 1-(tert-butoxycarbonyl)-(2S,4S)-4-(dibenzophospholyl)-2-[(dibenzophospholyl)methyl]-pyrrolidine, BINAPHOS, kelliphite, chiraphite, bis-3,4-diazophospholane; bis(phospholane) ligands, such as bis(2,5-trans-dialkylphospholane), bis(2,4-trans-dialkylphosphethane), 1,2-bis(phenoxyphosphine)ethane, 1,2-bis(3-methylphenoxyphosphine)ethane, 1,2-bis(2-methylphenoxyphosphine)ethane, 1,2-bis(1-methylphenoxyphosphine)ethane, 1,2-bis(1,3,5-trimethylphenoxyphosphine)ethan, 1,3-bis(phenoxyphosphine)propane, 1,3-bis(3-methylphenoxyphosphine)propane, 1,3-bis(2-methylphenoxyphosphine)propane, 1,3-bis(1-methylphenoxyphosphine)propane, 1,3-bis(1,3,5-trimethylphenoxyphosphine)propane, 1,4-bis(phenoxyphosphine)butane, 1,4-bis(3-methylphenoxyphosphine)butane, 1,4-bis(2-methylphenoxyphosphine)butane, 1,4-bis(1-methylphenoxyphosphine)butane, 1,4-bis(1,3,5-trimethylphenoxyphosphine)butane.

The proportion of catalyst C based on the monofunctionalized dialkylphosphinic acid (III) used is preferably in the range from 0.00001 to 20 mol % and more preferably in the range from 0.0001 to 10 mol %.

The hydrogenation reaction is preferably carried out in the presence of a promoter, preferred promoters being alkali and alkaline earth hydroxides and alkoxides. Examples of such promoters are NaOH, KOH, $Mg(OH)_2$, $Ca(OH)_2$, $Ba(OH)_2$ and also sodium methoxide, potassium methoxide, sodium ethoxide or sodium butoxide, of which NaOH and KOH are particularly preferred.

The ratio of promoter to catalyst is preferably about 0.001:1 to 0.5:1, more preferably about 0.01:1 to 0.2:1 and even more preferably 0.04:1 to 0.1:1.

Preferably, first at least a portion of the promoter and then the amine are added to the catalyst and/or the solution/suspension which the catalyst contains. The proportion of promoter added at first is preferably at least 10% by weight, more preferably 20% by weight and even more preferably 50% by weight.

It is particularly preferable to add 100% by weight of the promoter.

It is particularly preferable to use the transition metals in their zerovalent state.

Preferably, the heterogeneous catalyst is effective during the reaction as a suspension or bound to a solid phase.

Preferably, the reaction takes place in a solvent as a single-phase system in homogeneous or heterogeneous mixture and/or in the gas phase.

Suitable solvents are those mentioned above in process stage a).

The reaction is preferably carried out in a dialkylphosphinic acid/solvent molar ratio in the range from 1:10 000 to 1:0 and more preferably in a dialkylphosphinic acid/solvent molar ratio in the range from 1:50 to 1:1.

The reaction is preferably carried out at temperatures of 20 to 200° C. and more preferably at temperatures of 40 to 150° C., more particularly at temperatures of 60 to 100° C.

The reaction time is preferably in the range from 0.1 to 20 hours.

The reaction is preferably carried out under the partial pressure of the hydrogen and/or of the solvent.

The process step of the process of the present invention is preferably carried out at a partial pressure of the hydrogen in the range from 0.1 to 100 bar, more preferably 0.5 to 50 bar and more particularly 1 to 20 bar.

The process step of the process of the present invention is preferably carried out at an absolute pressure of 0.1 to 150 bar, more preferably 0.5 to 70 bar and more particularly 1 to 30 bar.

The hydrogenation of the present invention can be carried out in liquid phase, in the gas phase or else in supercritical phase. The catalyst is preferably used in the case of liquids in homogeneous form or as suspension, while a fixed bed arrangement is advantageous in the case of gas phase or supercritical operation.

When the compounds having C=X double bonds comprise C=N double bonds, those of the type $R^5R^6C=NR^7$ are preferred.

Preferred compounds of the type $R^5R^6C=NR^7$ are imines, such as hexamine, benzophenoneimine, 2,2,4,4-tetramethyl-3-pentanoneimine, N-benzylidenemethylamine and N-trimethylsilylbenzaldimine.

$R^7$ is preferably detached from the monofunctionalized dialkylphosphinic acids, esters or salts (III) by reaction with mineral acids or by reaction with hydrogen in the presence of a catalyst C.

Preferably, the transition metals for catalyst A comprise elements of the seventh and eighth transition groups (a metal of group 7, 8, 9 or 10, in modern nomenclature), for example rhenium, ruthenium, cobalt, rhodium, iridium, nickel, palladium and platinum.

Preference for use as source of the transition metals and transition metal compounds is given to their metal salts. Suitable salts are those of mineral acids containing the anions fluoride, chloride, bromide, iodide, fluorate, chlorate, bromate, iodate, fluorite, chlorite, bromite, iodite, hypofluorite, hypochlorite, hypobromite, hypoiodite, perfluorate, perchlorate, perbromate, periodate, cyanide, cyanate, nitrate, nitride, nitrite, oxide, hydroxide, borate, sulfate, sulfite, sulfide, persulfate, thiosulfate, sulfamate, phosphate, phosphite, hypophosphite, phosphide, carbonate and sulfonate, for example methanesulfonate, chlorosulfonate, fluorosulfonate, trifluoromethanesulfonate, benzenesulfonate, naphthylsulfonate, toluenesulfonate, t-butylsulfonate, 2-hydroxypropanesulfonate and sulfonated ion exchange resins; and/or organic salts, for example acetylacetonates and salts of a carboxylic acid having up to 20 carbon atoms, for example formate, acetate, propionate, butyrate, oxalate, stearate and citrate including halogenated carboxylic acids having up to 20 carbon atoms, for example trifluoroacetate, trichloroacetate.

A further source of the transition metals and transition metal compounds is salts of the transition metals with tetraphenylborate and halogenated tetraphenylborate anions, for example perfluorophenylborate.

Suitable salts similarly include double salts and complex salts consisting of one or more transition metal ions and independently one or more alkali metal, alkaline earth metal, ammonium, organic ammonium, phosphonium and organic phosphonium ions and independently one or more of the abovementioned anions. Examples of suitable double salts are ammonium hexachloropalladate and ammonium tetrachloropalladate.

Preference for use as a source of the transition metals is given to the transition metal as an element and/or a transition metal compound in its zerovalent state.

Preferably, the transition metal salt is used as a metal, or as an alloy with further metals, in which case boron, zirconium, tantalum, tungsten, rhenium, cobalt, iridium, nickel, palladium, platinum and/or gold is preferred here. The transition metal content in the alloy used is preferably 45-99.95% by weight.

Preferably, the transition metal is used in microdisperse form (particle size 0.1 mm-100 μm).

Preferably, the transition metal is used supported on a metal oxide such as, for example, alumina, silica, titanium dioxide, zirconium dioxide, zinc oxide, nickel oxide, vanadium oxide, chromium oxide, magnesium oxide, Celite®, diatomaceous earth, on a metal carbonate such as, for example, barium carbonate, calcium carbonate, strontium carbonate, on a metal sulfate such as, for example, barium sulfate, calcium sulfate, strontium sulfate, on a metal phosphate such as, for example, aluminum phosphate, vanadium phosphate, on a metal carbide such as, for example, silicone carbide, on a metal aluminate such as, for example, calcium aluminate, on a metal silicate such as, for example, aluminum silicate, chalks, zeolites, bentonite, montmorillonite, hectorite, on functionalized silicates, functionalized silica gels such as, for example, SiliaBond®, QuadraSil™, on functionalized polysiloxanes such as, for example, Deloxan®, on a metal nitride, on carbon, activated carbon, mullite, bauxite, antimonite, scheelite, perovskite, hydrotalcite, heteropolyanions, on functionalized and unfunctionalized cellulose, chitosan, keratin, heteropolyanions, on ion exchangers such as, for example, Amberlite™, Amberjet™, Ambersep™, Dowex®, Lewatit®, ScavNet®, on functionalized polymers such as, for example, Chelex®, QuadraPure™, Smopex®, PolyOrgs®, on polymer-bound phosphanes, phosphane oxides, phosphinates, phosphonates, phosphates, amines, ammonium salts, amides, thioamides, ureas, thioureas, triazines, imidazoles, pyrazoles, pyridines, pyrimidines, pyrazines, thiols, thiol ethers, thiol esters, alcohols, alkoxides, ethers, esters, carboxylic acids, acetates, acetals, peptides, hetarenes, polyethyleneimine/silica and/or dendrimers.

Suitable sources for the metal salts and/or transition metals likewise preferably include their complex compounds. Complex compounds of the metal salts and/or transition metals are composed of the metal salts/transition metals and one or more complexing agents. Suitable complexing agents include for example olefins, diolefins, nitriles, dinitriles, carbon monoxide, phosphines, diphosphines, phosphites, diphosphites, dibenzylideneacetone, cyclopentadienyl, indenyl or styrene. Suitable complex compounds of the metal salts and/or transition metals may be supported on the abovementioned support materials.

The proportion in which the supported transition metals mentioned are present is preferably in the range from 0.01% to 20% by weight, more preferably from 0.1% to 10% by weight and even more preferably from 0.2% to 5% by weight, based on the total mass of the support material.

Suitable sources for transition metals and transition metal compounds include for example palladium, platinum, nickel, rhodium; palladium platinum, nickel or rhodium, on alumina, on silica, on barium carbonate, on barium sulfate, on calcium carbonate, on strontium carbonate, on carbon, on activated carbon; platinum-palladium-gold alloy, aluminum-nickel alloy, iron-nickel alloy, lanthanide-nickel alloy, zirconium-nickel alloy, platinum-iridium alloy, platinum-rhodium alloy; Raney® nickel, nickel-zinc-iron oxide; palladium(II) chloride, palladium(II) bromide, palladium(II) iodide, palladium(II) fluoride, palladium(II) hydride, palladium(II) oxide, palladium(II) peroxide, palladium(II) cyanide, palladium(II) sulfate, palladium(II) nitrate, palladium(II) phosphide, palladium(II) boride, palladium(II) chromium oxide, palladium(II) cobalt oxide, palladium(II) carbonate hydroxide, palladium(II) cyclohexane butyrate, palladium(II) hydroxide, palladium(II) molybdate, palladium(II) octanoate, palladium(II) oxalate, palladium(II) perchlorate, palladium(II) phthalocyanine, palladium(II) 5,9,14,18,23,27,32,36-octabutoxy-2,3-naphthalocyanine, palladium(II) sulfamate, palladium(II) perchlorate, palladium(II) thiocyanate, palladium(II) bis(2,2,6,6-tetramethyl-3,5-heptanedionate), palladium(II) propionate, palladium(II) acetate, palladium(II) stearate, palladium(II) 2-ethylhexanoate, palladium(II) acetylacetonate, palladium(II) hexafluoroacetylacetonate, palladium(II) tetrafluoroborate, palladium(II) thiosulfate, palladium(II) trifluoroacetate, palladium(II) phthalocyaninetetrasulfonic acid tetrasodium salt, palladium(II) methyl, palladium(II) cyclopentadienyl, palladium(II) methylcyclopentadienyl, palladium(II) ethylcyclopentadienyl, palladium(II) pentamethylcyclopentadienyl, palladium(II) 2,3,7,8,12,13,17,18-octaethyl-21H,23H-porphine, palladium(II) 5,10,15,20-tetraphenyl-21H,23H-porphine, palladium(II) bis(5-[[4-(dimethylamino)phenyl]imino]-8(5H)-quinolinone), palladium(II) 2,11,20,29-tetra-tert-butyl-2,3-naphthalocyanine, palladium(II) 2,9,16,23-tetraphenoxy-29H,31H-phthalocyanine, palladium(II) 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenyl)imidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesityl)imidazol-2-ylidene, bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2"-terpyridine, diethyl sulfide, ethylene and amine complexes thereof;

nickel(II) chloride, nickel(II) bromide, nickel(II) iodide, nickel(II) fluoride, nickel(II) hydride, nickel(II) oxide, nickel(II) peroxide, nickel(II) cyanide, nickel(II) sulfate, nickel(II) nitrate, nickel(II) phosphide, nickel(II) boride, nickel(II) chromium oxide, nickel(II) cobalt oxide, nickel(II) carbonate hydroxide, nickel(II) cyclohexane butyrate, nickel(II) hydroxide, nickel(II) molybdate, nickel(II) octanoate, nickel(II) oxalate, nickel(II) perchlorate, nickel(II) phthalocyanine, nickel(II) 5,9,14,18,23,27,32,36-octabutoxy-2,3-naphthalocyanine, nickel(II) sulfamate, nickel(II) perchlorate, nickel(II) thiocyanate, nickel(II) bis(2,2,6,6-tetramethyl-3,5-heptanedionate), nickel(II) propionate, nickel(II) acetate, nickel(II) stearate, nickel(II) 2-ethylhexanoate, nickel(II) acetylacetonate, nickel(II) hexafluoroacetylacetonate, nickel(II) tetrafluoroborate, nickel(II) thiosulfate, nickel(II) trifluoroacetate, nickel(II) phthalocyaninetetrasulfonic acid tetrasodium salt, nickel(II) methyl, nickel(II) cyclopentadienyl, nickel(II) methylcyclopentadienyl, nickel(II) ethylcyclopentadienyl, nickel(II) pentamethylcyclopentadienyl, nickel(II) 2,3,7,8,12,13,17,18-octaethyl-21H,23H-porphine, nickel(II) 5,10,15,20-tetraphenyl-21H,23H-porphine, nickel(II) bis(5-[[4-(dimethylamino)phenyl]imino]-8(5H)-quinolinone), nickel(II) 2,11,20,29-tetra-tert-butyl-2,3-naphthalocyanine, nickel(II) 2,9,16,23-tetraphenoxy-29H,31H-phthalocyanine, nickel(II) 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenyl)imidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesityl)imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2"-terpyridine, diethyl sulfide, ethylene and amine complexes thereof;

platinum(II) chloride, platinum(II) bromide, platinum(II) iodide, platinum(II) fluoride, platinum(II) hydride, platinum(II) oxide, platinum(II) peroxide, platinum(II) cyanide, platinum(II) sulfate, platinum(II) nitrate, platinum(II) phosphide, platinum(II) boride, platinum(II) chromium oxide, platinum(II) cobalt oxide, platinum(II) carbonate hydroxide, platinum(II) cyclohexane butyrate, platinum(II) hydroxide, platinum(II) molybdate, platinum(II) octanoate, platinum(II) oxalate, platinum(II) perchlorate, platinum(II) phthalocyanine, platinum(II) 5,9,14,18,23,27,32,36-octabutoxy-2,3-naphthalocyanine, platinum(II) sulfamate, platinum(II) perchlorate, platinum(II) thiocyanate, platinum(II) bis(2,2,6,6-tetramethyl-3,5-heptanedionate), platinum(II) propionate, platinum(II) acetate, platinum(II) stearate, platinum(II) 2-ethylhexanoate, platinum(II) acetylacetonate, platinum(II) hexafluoroacetylacetonate, platinum(II) tetrafluoroborate, platinum(II) thiosulfate, platinum(II) trifluoroacetate, platinum(II) phthalocyaninetetrasulfonic acid tetrasodium salt, platinum(II) methyl, platinum(II) cyclopentadienyl, platinum(II) methylcyclopentadienyl, platinum(II) ethylcyclopentadienyl, platinum(II) pentamethylcyclopentadienyl, platinum(II) 2,3,7,8,12,13,17,18-octaethyl-21H,23H-porphine, platinum(II) 5,10,15,20-tetraphenyl-21H,23H-porphine, platinum(II) bis(5-[[4-(dimethylamino)phenyl]imino]-8(5H)-quinolinone), platinum(II) 2,11,20,29-tetra-tert-butyl-2,3-naphthalocyanine, platinum(II) 2,9,16,23-tetraphenoxy-29H,31H-phthalocyanine, platinum(II) 5,10,15,20-tetrakis (pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenyl)imidazolidene)(3-chloropyridyl), 2'-(dimethylamino)-2-biphenylyl, dinorbornylphosphine, 2-(dimethylamino-methyl)ferrocene, allyl, bis(diphenylphosphino)butane, (N-succinimidyl)bis-(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesityl)imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2''-terpyridine, diethyl sulfide, ethylene and amine complexes thereof;

rhodium chloride, rhodium bromide, rhodium iodide, rhodium fluoride, rhodium hydride, rhodium oxide, rhodium peroxide, rhodium cyanide, rhodium sulfate, rhodium nitrate, rhodium phosphide, rhodium boride, rhodium chromium oxide, rhodium cobalt oxide, rhodium carbonate hydroxide, rhodium cyclohexane butyrate, rhodium hydroxide, rhodium molybdate, rhodium octanoate, rhodium oxalate, rhodium perchlorate, rhodium phthalocyanine, rhodium 5,9,14,18,23,27,32,36-octabutoxy-2,3-naphthalocyanine, rhodium sulfamate, rhodium perchlorate, rhodium thiocyanate, rhodium bis(2,2,6,6-tetramethyl-3,5-heptanedionate), rhodium propionate, rhodium acetate, rhodium stearate, rhodium 2-ethylhexanoate, rhodium acetylacetonate, rhodium hexafluoroacetylacetonate, rhodium tetrafluoroborate, rhodium thiosulfate, rhodium trifluoroacetate, rhodium phthalocyaninetetrasulfonic acid tetrasodium salt, rhodium methyl, rhodium cyclopentadienyl, rhodium methylcyclopentadienyl, rhodium ethylcyclopentadienyl, rhodium pentamethylcyclopentadienyl, rhodium 2,3,7,8,12,13,17,18-octaethyl-21H,23H-porphine, rhodium 5,10,15,20-tetraphenyl-21H,23H-porphine, rhodium bis(5-[[4-(dimethylamino)phenyl]imino]-8(5H)-quinolinone), rhodium 2,11,20,29-tetra-tert-butyl-2,3-naphthalocyanine, rhodium 2,9,16,23-tetraphenoxy-29H,31H-phthalocyanine, rhodium 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenyl)imidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesityl)imidazol-2-ylidene, bis(diphenylphosphino)ferrocene, bis(diphenylphosphino)ethane, N-methylimidazole, 2,2'-bipyridine, (bicyclo[2.2.1]hepta-2,5-diene), bis(di-tert-butyl(4-dimethylaminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2''-terpyridine, diethyl sulfide, ethylene and amine complexes thereof;

potassium hexachloropalladate(IV), sodium hexachloropalladate(IV), ammonium hexachloropalladate(IV), potassium tetrachloropalladate(II), sodium tetrachloropalladate(II), ammonium tetrachloropalladate(II), bromo(tri-tert-butylphosphine)palladium(I) dimer, (2-methylallyl)palladium(II) chloride dimer, bis(dibenzylideneacetone)palladium(0), tris(dibenzylideneacetone)dipalladium(0), tetrakis(triphenylphosphine)palladium(0), tetrakis(tricyclohexylphosphine)-palladium(0), bis[1,2-bis(diphenylphosphine)ethane]palladium(0), bis(3,5,3',5'-dimethoxydibenzylideneacetone)palladium(0), bis(tri-tert-butylphosphine)palladium(0), meso-tetraphenyltetrabenzoporphinepalladium, tetrakis(methyldiphenylphosphine)palladium(0), tris(3,3',3''-phophinidyne-tris(benzenesulfonato)palladium(0) nonasodium salt, 1,3-bis(2,4,6-trimethylphenyl)imidazol-2-ylidene(1,4-naphthoquinone)palladium(0), 1,3-bis(2,6-diisopropylphenyl)imidazol-2-ylidene(1,4-naphthoquinone) palladium(0) and the chloroform complex thereof;

allylnickel(II) chloride dimer, ammoniumnickel(II) sulfate, bis(1,5-cyclooctadiene)nickel(0), bis(triphenylphosphine)dicarbonylnickel(0), tetrakis(triphenylphosphine)nickel(0), tetrakis(triphenyl phosphite)nickel(0), potassium hexafluoronickelate(IV), potassium tetracyanonickelate(II), potassium nickel(IV) paraperiodate, dilithium tetrabromonickelate(II), potassium tetracyanonickelate(II); platinum(IV) chloride, platinum(IV) oxide, platinum(IV) sulfide, potassium hexachloroplatinate(IV), sodium hexachloroplatinate(IV), ammonium hexachloroplatinate(IV), potassium tetrachloroplatinate(II), ammonium tetrachloroplatinate(II), potassium tetracyanoplatinate(II), trimethyl(methylcyclopentadienyl)platinum(IV), cis-diammintetrachloroplatinum(IV), potassium trichloro(ethylene)platinate(II), sodium hexahydroxyplatinate(IV), tetraamineplatinum(II) tetrachloroplatinate(II), tetrabutylammonium hexachloroplatinate(IV), ethylenebis(triphenylphosphine)platinum(0), platinum(0) 1,3-divinyl-1,1,3,3-tetramethyldisiloxane, platinum(0) 2,4,6,8-tetramethyl-2,4,6,8-tetravinylcyclotetrasiloxane, tetrakis(triphenylphosphine)platinum(0), platinum octaethylporphyrine, chloroplatinic acid, carboplatin;

chlorobis(ethylene)rhodium dimer, hexarhodium hexadecacarbonyl, chloro(1,5-cyclooctadiene)rhodium dimer, chloro(norbornadiene)rhodium dimer, chloro(1,5-hexadiene)rhodium dimer.

The ligands preferably comprise phosphines of the formula (V)

$$PR^{11}_3 \quad (V)$$

where the $R^{11}$ radicals are each independently hydrogen, straight-chain, branched or cyclic $C_1$-$C_{20}$-alkyl, $C_6$-$C_{20}$-alkylaryl, $C_2$-$C_{20}$-alkenyl, $C_2$-$C_{20}$-alkynyl, $C_1$-$C_{20}$-carboxylate, $C_1$-$C_{20}$-alkoxy, $C_2$-$C_{20}$-alkenyloxy, $C_2$-$C_{20}$-alkynyloxy, $C_2$-$C_{20}$-alkoxycarbonyl, $C_1$-$C_{20}$-alkylthio, $C_1$-$C_{20}$-alkylsulfonyl, $C_1$-$C_{20}$-alkylsulfinyl, silyl and/or their derivatives and/or phenyl substituted by at least one $R^{12}$, or naphthyl substituted by at least one $R^{12}$. $R^{12}$ in each occurrence is independently hydrogen, fluorine, chlorine, bromine, iodine, $NH_2$, nitro, hydroxyl, cyano, formyl, straight-chain, branched or cyclic $C_1$-$C_{20}$-alkyl, $C_1$-$C_{20}$-alkoxy, $HN(C_1$-$C_{20}$-alkyl), $N(C_1$-$C_{20}$-alkyl)$_2$, —$CO_2$—($C_1$-$C_{20}$-alkyl), —$CON(C_1$-$C_{20}$-alkyl)$_2$, —$OCO(C_1$-$C_{20}$-alkyl), $NHCO(C_1$-$C_{20}$-alkyl), $C_1$-$C_{20}$-Acyl, —$SO_3M$, —$SO_2N(R^{13})M$, —$CO_2M$, —PO$_3$M$_2$, —AsO$_3$M$_2$, —SiO$_2$M, —C(CF$_3$)$_2$OM (M=H, Li, Na or K), where R$^{13}$ is hydrogen, fluorine, chlorine, bromine, iodine, straight-chain, branched or cyclic C$_1$-C$_{20}$-alkyl, C$_2$-C$_{20}$-alkenyl, C$_2$-C$_{20}$-alkynyl, C$_1$-C$_{20}$-carboxylate, C$_1$-C$_{20}$-alkoxy, C$_2$-C$_{20}$-alkenyloxy, C$_2$-C$_{20}$-alkynyloxy, C$_2$-C$_{20}$-alkoxycarbonyl, C$_1$-C$_{20}$-alkylthio, C$_1$-C$_{20}$-alkylsulfonyl, C$_1$-C$_{20}$-alkylsulfinyl, silyl and/or their derivatives, aryl, C$_6$-C$_{20}$-arylalkyl, C$_6$-C$_{20}$-alkylaryl, phenyl and/or biphenyl. Preferably, the R$^{11}$ groups are all identical.

Suitable phosphines(V) are for example trimethylphosphine, triethylphosphine, tripropylphosphine, triisopropylphosphine, tributylphosphine, triisobutylphosphine, triisopentylphosphine, trihexylphosphine, tricyclohexylphosphine, trioctylphosphine, tridecylphosphine, triphenylphosphine, diphenylmethylphosphine, phenyldimethylphosphine, tri(o-tolyl)phosphine, tri(p-tolyl)phosphine, ethyldiphenylphosphine, dicyclohexylphenylphosphine, 2-pyridyl-diphenylphosphine, bis(6-methyl-2-pyridyl)phenylphosphine, tri(p-chlorophenyl)-phosphine, tri(p-methoxyphenyl)phosphine, diphenyl(2-sulfonatophenyl)-phosphine; potassium, sodium and ammonium salts of diphenyl(3-sulfonatophenyl)phosphine, bis(4,6-dimethyl-3-sulfonatophenyl)(2,4-dimethylphenyl)phosphine, bis(3-sulfonatophenyl)phenylphosphines, tris(4,6-dimethyl-3-sulfonatophenyl)phosphines, tris(2-sulfonatophenyl)phosphines, tris(3-sulfonatophenyl)phosphines; 2-bis(diphenylphosphinoethyl)trimethylammonium iodide, 2'-dicyclohexylphosphino-2,6-dimethoxy-3-sulfonato-1,1'-biphenyl sodium salt, trimethyl phosphite and/or triphenyl phosphite.

The ligands more preferably comprise bidentate ligands of the general formula

$$R^{11}M''\text{-}Z\text{-}M''R^{11} \qquad (VI).$$

In this formula, each M" independently is N, P, As or Sb. M" is preferably the same in the two occurrences and more preferably is a phosphorus atom.

Each R$^{11}$ group independently represents the radicals described under formula (V). The R$^{11}$ groups are preferably all identical.

Z is preferably a bivalent bridging group which contains at least 1 bridging atom, preferably from 2 to 6 bridging atoms.

Bridging atoms can be selected from carbon, nitrogen, oxygen, silicon and sulfur atoms. Z is preferably an organic bridging group containing at least one carbon atom. Z is preferably an organic bridging group containing 1 to 6 bridging atoms, of which at least two are carbon atoms, which may be substituted or unsubstituted.

Preferred Z groups are —CH$_2$—, —CH$_2$—CH$_2$—, —CH$_2$—CH$_2$—CH$_2$—, —CH$_2$—CH(CH$_3$)—CH$_2$—, —CH$_2$—C(CH$_3$)$_2$—CH$_2$—, —CH$_2$—C(C$_2$H$_5$)—CH$_2$—, —CH$_2$—Si(CH$_3$)$_2$—CH$_2$—, —CH$_2$—CH$_2$—CH$_2$—CH$_2$—, —CH$_2$—CH(C$_2$H$_5$)—CH$_2$—, —CH$_2$—CH(n-Pr)—CH and —CH$_2$—CH(n-Bu)-CH$_2$—, substituted or unsubstituted 1,2-phenyl, 1,2-cyclohexyl, 1,1'- or 1,2-ferrocenyl radicals, 2,2'-(1,1'-biphenyl), 4,5-xanthene and/or oxydi-2,1-phenylene radicals.

Examples of suitable bidentate phosphine ligands (VI) are for example 1,2-bis(dimethylphosphino)ethane, 1,2-bis(diethylphosphino)ethane, 1,2-bis(dipropylphosphino)ethane, 1,2-bis(diisopropylphosphino)ethane, 1,2-bis(dibutylphosphino)ethane, 1,2-bis(di-tert-butylphosphino)ethane, 1,2-bis(dicyclohexylphosphino)ethane, 1,2-bis(diphenylphosphino)ethane; 1,3-bis(dicyclohexylphosphino)propane, 1,3-bis(diisopropylphosphino)propane, 1,3-bis(di-tert-butylphosphino)propane, 1,3-bis(diphenylphosphino)propane; 1,4-bis(diisopropylphosphino)butane, 1,4-bis(diphenylphosphino)butane; 1,5-bis(dicyclohexylphosphino)pentane; 1,2-bis(di-tert-butylphosphino)benzene, 1,2-bis(diphenylphosphino)benzene, 1,2-bis(dicyclohexylphosphino)benzene, 1,2-bis(dicyclopentylphosphino)benzene, 1,3-bis(di-tert-butylphosphino)benzene, 1,3-bis(diphenylphosphino)benzene, 1,3-bis(dicyclohexylphosphino)benzene, 1,3-bis(dicyclopentylphosphino)benzene; 9,9-dimethyl-4,5-bis(diphenylphosphino)-xanthene, 9,9-dimethyl-4,5-bis(diphenylphosphino)-2,7-di-tert-butylxanthene, 9,9-dimethyl-4,5-bis(di-tert-butylphosphino)xanthene, 1,1'-bis(diphenylphosphino)-ferrocene, 2,2'-bis(diphenylphosphino)-1,1'-binaphthyl, 2,2'-bis(di-p-tolylphosphino)-1,1'-binaphthyl, (oxydi-2,1-phenylene)bis(diphenylphosphine), 2,5-(diisopropylphospholano)benzene, 2,3-O-isopropylidene-2,3-dihydroxy-1,4-bis(diphenylphosphino)butane, 2,2'-bis(di-tert-butylphosphino)-1,1-biphenyl, 2,2'-bis(dicyclohexylphosphino)-1,1'-biphenyl, 2,2'-bis(diphenylphosphino)-1,1'-biphenyl, 2-(di-tert-butylphosphino)-2'-(N,N-dimethylamino)biphenyl, 2-(dicyclohexylphosphino)-2'-(N,N-dimethylamino)biphenyl, 2-(diphenylphosphino)-2'-(N,N-dimethylamino)biphenyl, 2-(diphenylphosphino)ethylamine, 2-[2-(diphenylphosphino)ethyl]pyridine; potassium, sodium and ammonium salts of 1,2-bis(di-4-sulfonatophenylphosphino)benzene, (2,2'-bis[[bis(3-sulfonatophenyl)phosphino]methyl]-4,4',7,7'-tetrasulfonato-1,1'-binapthyl, (2,2'-bis[[bis(3-sulfonatophenyl)phosphino]methyl]-5,5'-tetrasulfonato-1,1'-biphenyl, (2,2'-bis[[bis(3-sulfonatophenyl)phosphino]methyl]-1,1'-binapthyl, (2,2'-bis[[bis(3-sulfonatophenyl)phosphino]methyl]-1,1'-biphenyl, 9,9-dimethyl-4,5-bis(diphenylphosphino)-2,7-sulfonatoxanthene, 9,9-dimethyl-4,5-bis(di-tert-butylphosphino)-2,7-sulfonatoxanthene, 1,2-bis(di-4-sulfonatophenylphosphino)-benzene, meso-tetrakis(4-sulfonatophenyl)porphine, meso-tetrakis(2,6-dichloro-3-sulfonatophenyl)porphine, meso-tetrakis(3-sulfonatomesityl)porphine, tetrakis(4-carboxyphenyl)porphine and 5,11,17,23-sulfonato-25,26,27,28-tetrahydroxycalix[4]arene.

Moreover, the ligands of the formula (V) and (VI) can be attached to a suitable polymer or inorganic substrate by the R$^{11}$ radicals and/or the bridging group.

The molar transition metal/ligand ratio of the catalyst system is in the range 1:0.01 to 1:100, preferably in the range from 1:0.05 to 1:10 and more preferably in the range from 1:1 to 1:4.

The reactions in the process stages a), b) and optionally c) preferably take place, if desired, in an atmosphere comprising further gaseous constituents such as nitrogen, oxygen, argon, carbon dioxide for example; the temperature is in the range from −20 to 340° C., more particularly in the range from 20 to 180° C., and total pressure is in the range from 1 to 100 bar.

The products and/or the components and/or the transition metal and/or the transition metal compound and/or catalyst system and/or the ligand and/or starting materials are optionally isolated after the process stages a), b) and c) by distillation or rectification, by crystallization or precipitation, by filtration or centrifugation, by adsorption or chromatography or other known methods.

According to the present invention, solvents, auxiliaries and any other volatile constituents are removed by distillation, filtration and/or extraction for example.

The reactions in the process stages a), b) and optionally c) are preferably carried out, if desired, in absorption columns, spray towers, bubble columns, stirred tanks, trickle bed reactors, flow tubes, loop reactors and/or kneaders.

Suitable mixing elements include for example anchor, blade, MIG, propeller, impeller and turbine stirrers, cross beaters, disperser disks, hollow (sparging) stirrers, rotor-stator mixers, static mixers, Venturi nozzles and/or mammoth pumps.

The intensity of mixing experienced by the reaction solutions/mixtures preferably corresponds to a rotation Reynolds number in the range from 1 to 1 000 000 and preferably in the range from 100 to 100 000.

It is preferable for an intensive commixing of the respective reactants etc. to be effected by an energy input in the range from 0.080 to 10 kW/m$^3$, preferably 0.30-1.65 kW/m$^3$.

During the reaction, the particular catalyst A is preferably homogeneous and/or heterogeneous in action. Therefore, the particular heterogeneous catalyst is effective during the reaction as a suspension or bound to a solid phase.

Preferably, the catalyst A is generated in situ before the reaction and/or at the start of the reaction and/or during the reaction.

Preferably, the particular reaction takes place in a solvent as a single-phase system in homogeneous or heterogeneous mixture and/or in the gas phase.

When a multi-phase system is used, a phase transfer catalyst may be used in addition.

The reactions of the present invention can be carried out in liquid phase, in the gas phase or in supercritical phase. The catalyst A is preferably used in the case of liquids in homogeneous form or as a suspension, while a fixed bed arrangement is advantageous in the case of gas phase or supercritical operation.

Suitable solvents for the methods of the present invention are water, alcohols, e.g. methanol, ethanol, isopropanol, n-propanol, n-butanol, isobutanol, tert-butanol, n-amyl alcohol, isoamyl alcohol, tert-amyl alcohol, n-hexanol, n-octanol, isooctanol, n-tridecanol, benzyl alcohol, etc. Preference is further given to glycols, e.g. ethylene glycol, 1,2-propanediol, 1,3-propanediol, 1,3-butanediol, 1,4-butanediol, diethylene glycol etc.; aliphatic hydrocarbons, such as pentane, hexane, heptane, octane, and petroleum ether, naphtha, kerosene, petroleum, paraffin oil, etc.; aromatic hydrocarbons, such as benzene, toluene, xylene, mesitylene, ethylbenzene, diethylbenzene, etc.; halogenated hydrocarbons, such as methylene chloride, chloroform, 1,2-dichloroethane, chlorobenzene, carbon tetrachloride, tetrabromoethylene, etc.; alicyclic hydrocarbons, such as cyclopentane, cyclohexane, and methylcyclohexane, etc.; ethers, such as anisole (methyl phenyl ether), tert-butyl methyl ether, dibenzyl ether, diethyl ether, dioxane, diphenyl ether, methyl vinyl ether, tetrahydrofuran, triisopropyl ether etc.; glycol ethers, such as diethylene glycol diethyl ether, diethylene glycol dimethyl ether (diglyme), diethylene glycol monobutyl ether, diethylene glycol monomethyl ether, 1,2-dimethoxyethane (DME, monoglyme), ethylene glycol monobutyl ether, triethylene glycol dimethyl ether (triglyme), triethylene glycol monomethyl ether etc.; ketones, such as acetone, diisobutyl ketone, methyl n-propyl ketone; methyl ethyl ketone, methyl isobutyl ketone etc.; esters, such as methyl formate, methyl acetate, ethyl acetate, n-propyl acetate, and n-butyl acetate, etc.; carboxylic acids, such as formic acid, acetic acid, propionic acid, butyric acid, etc. One or more of these compounds can be used, alone or in combination.

Suitable solvents also encompass the phosphinic acid sources and olefins used. These have advantages in the form of higher space-time yield.

It is preferable that the reaction be carried out under the autogenous vapor pressure of the olefin and/or of the solvent.

Preferably, $R^1$, $R^2$, $R^3$ and $R^4$ of olefin (IV) are the same or different and each is independently H, methyl, ethyl, n-propyl, isopropyl, n-butyl, isobutyl, tert-butyl and/or phenyl.

Preference is also given to using functionalized olefins such as allyl isothiocyanate, allyl methacrylate, 2-allylphenol, N-allylthiourea, 2-(allylthio)-2-thiazoline, allyltrimethylsillane, allyl acetate, allyl acetoacetate, allyl alcohol, allylamine, allylbenzene, allyl cyanide, allyl cyanoacetate, allylanisole, trans-2-pentenal, cis-2-pentenenitrile, 1-penten-3-ol, 4-penten-1-ol, 4-penten-2-ol, trans-2-hexenal, trans-2-hexen-1-ol, cis-3-hexen-1-ol, 5-hexen-1-ol, styrene, -methylstyrene, 4-methylstyrene, vinyl acetate, 9-vinylanthracene, 2-vinylpyridine, 4-vinylpyridine and 1-vinyl-2-pyrrolidone.

The partial pressure of the olefin during the reaction is preferably 0.01-100 bar and more preferably 0.1-10 bar.

The phosphinic acid/olefin molar ratio for the reaction is preferably in the range from 1:10 000 to 1:0.001 and more preferably in the range from 1:30 to 1:0.01.

The phosphinic acid/catalyst molar ratio for the reaction is preferably in the range from 1:1 to 1:0.00000001 and more preferably in the range from 1:0.01 to 1:0.000001.

The phosphinic acid/solvent molar ratio for the reaction is preferably in the range from 1:10 000 to 1:0 and more preferably in the range from 1:50 to 1:1.

One method the present invention provides for producing compounds of the formula (II) comprises reacting a phosphinic acid source with olefins in the presence of a catalyst and freeing the product (II) (alkylphosphonous acid, salts or esters) of catalyst, transition metal or transition metal compound as the case may be, ligand, complexing agent, salts and by-products.

The present invention provides that the catalyst, the catalyst system, the transition metal and/or the transition metal compound are separated off by adding an auxiliary 1 and removing the catalyst, the catalyst system, the transition metal and/or the transition metal compound by extraction and/or filtration.

The present invention provides that the ligand and/or complexing agent is separated off by extraction with auxiliary 2 and/or distillation with auxiliary 2.

Auxiliary 1 is preferably water and/or at least one member of the group of metal scavengers. Preferred metal scavengers are metal oxides, such as aluminum oxide, silicon dioxide, titanium dioxide, zirconium dioxide, zinc oxide, nickel oxide, vanadium oxide, chromium oxide, magnesium oxide, Celite®, kieselguhr; metal carbonates, such as barium carbonate, calcium carbonate, strontium carbonate; metal sulfates, such as barium sulfate, calcium sulfate, strontium sulfate; metal phosphates, such as aluminum phosphate, vanadium phosphate, metal carbides, such as silicone carbide; metal aluminates, such as calcium aluminate; metal silicates, such as aluminum silicate, chalks, zeolites, bentonite, montmorillonite, hectorite; functionalized silicates, functionalized silica gels, such as SiliaBond®, QuadraSil™; functionalized polysiloxanes, such as Deloxan®; metal nitrides, carbon, activated carbon, mullite, bauxite, antimonite, scheelite, perovskite, hydrotalcite, functionalized and unfunctionalized cellulose, chitosan, keratin, heteropolyanions, ion exchangers, such as Amberlite™, Amberjet™, Ambersep™, Dowex®, Lewatit®, ScavNet®; functionalized polymers, such as Chelex®, QuadraPure™, Smopex®, Poly-Orgs®; polymer-bound phosphanes, phosphane oxides, phosphinates, phosphonates, phosphates, amines, ammonium salts, amides, thioamides, urea, thioureas, triazines, imidazoles, pyrazoles, pyridines, pyrimidines, pyrazines, thiols, thiol ethers, thiol esters, alcohols, alkoxides, ethers, esters, carboxylic acids, acetates, acetals, peptides, hetarenes, polyethyleneimine/silicon dioxide, and/or dendrimers.

It is preferable that the amounts added of auxiliary 1 correspond to 0.1-40% by weight loading of the metal on auxiliary 1.

It is preferable that auxiliary 1 be used at temperatures of from 20 to 90° C.

It is preferable that the residence time of auxiliary 1 be from 0.5 to 360 minutes.

Auxiliary 2 is preferably the aforementioned solvent of the present invention.

In step b), the molar ratio of compounds having C=X double bonds to alkylphosphonous acid (II) is in the range from 0.5:1 to 10:1 and more particularly in the range from 1:1 to 5:1.

The reaction in step b) of the method of the present invention is preferably carried out at a ratio of solvent to alkylphosphonous acid (II) in the range from 100:1 to 1:10.

The esterification of the monofunctionalized dialkylphosphinic acid (III) or of the alkylphosphonous acid derivatives (II) and also of the phosphinic acid source (I) to form the corresponding esters can be achieved for example by reaction with higher-boiling alcohols by removing the resultant water by azeotropic distillation, or by reaction with epoxides (alkylene oxides).

M-OH preferably comprises primary, secondary or tertiary alcohols having a carbon chain length of $C_1$-$C_{18}$. Particular preference is given to methanol, ethanol, propanol, isopropanol, n-butanol, 2-butanol, tert-butanol, amyl alcohol and/or hexanol.

M'-OH preferably comprises ethylene glycol, 1,2-propylene glycol, 1,3-propylene glycol, 1,4-butanediol, 2,2-dimethylpropane-1,3-diol, neopentyl glycol, 1,6-hexanediol, 1,4-cyclohexanedimethanol, glycerol, trishydroxymethylethane, trishydroxymethylpropane, pentaerythritol, sorbitol, mannitol, α-naphthol, polyethylene glycols, polypropylene glycols and/or EO-PO block polymers.

Also useful as M-OH and M'-OH are mono- or polyhydric unsaturated alcohols having a carbon chain length of $C_1$-$C_{18}$, for example n-but-2-en-1-ol, 1,4-butenediol and allyl alcohol.

Also useful as M-OH and M'-OH are reaction products of monohydric alcohols with one or more molecules of alkylene oxides, preferably with ethylene oxide and/or 1,2-propylene oxide. Preference is given to 2-methoxyethanol, 2-ethoxyethanol, 2-n-butoxyethanol, 2-(2'-ethylhexyloxy)ethanol, 2-n-dodecoxyethanol, methyl diglycol, ethyl diglycol, isopropyl diglycol, fatty alcohol polyglycol ethers and aryl polyglycol ethers.

M-OH and M'-OH are also preferably reaction products of polyhydric alcohols with one or more molecules of alkylene oxide, more particularly diglycol and triglycol and also adducts of 1 to 6 molecules of ethylene oxide or propylene oxide onto glycerol, trishydroxymethylpropane or pentaerythritol.

Useful M-OH and M'-OH further include reaction products of water with one or more molecules of alkylene oxide. Preference is given to polyethylene glycols and poly-1,2-propylene glycols of various molecular sizes having an average molecular weight of 100-1000 g/mol and more preferably of 150-350 g/mol.

Preference for use as M-OH and M'-OH is also given to reaction products of ethylene oxide with poly-1,2-propylene glycols or fatty alcohol propylene glycols; similarly reaction products of 1,2-propylene oxide with polyethylene glycols or fatty alcohol ethoxylates. Preference is given to such reaction products with an average molecular weight of 100-1000 g/mol, more preferably of 150-450 g/mol.

Also useful as M-OH and M'-OH are reaction products of alkylene oxides with ammonia, primary or secondary amines, hydrogen sulfide, mercaptans, oxygen acids of phosphorus and $C_2$-$C_6$ dicarboxylic acids. Suitable reaction products of ethylene oxide with nitrogen compounds are triethanolamine, methyldiethanolamine, n-butyldiethanolamine, n-dodecyldiethanolamine, dimethylethanolamine, n-butylmethylethanolamine, di-n-butylethanolamine, n-dodecylmethylethanolamine, tetrahydroxyethylethylenediamine or pentahydroxyethyldiethylenetriamine.

Preferred alkylene oxides are ethylene oxide, 1,2-propylene oxide, 1,2-epoxybutane, 1,2-epoxyethylbenzene, (2,3-epoxypropyl)benzene, 2,3-epoxy-1-propanol and 3,4-epoxy-1-butene.

Suitable solvents are the solvents mentioned in process step a) and also the M-OH and M'-OH alcohols used and the alkylene oxides. These offer advantages in the form of a higher space-time yield.

The reaction is preferably carried out under the autogenous vapor pressure of the employed alcohol M-OH, M'-OH and alkylene oxide and/or of the solvent.

Preferably, the reaction is carried out at a partial pressure of the employed alcohol M-OH, M'-OH and alkylene oxide of 0.01-100 bar, more preferably at a partial pressure of the alcohol of 0.1-10 bar.

The reaction is preferably carried out at a temperature in the range from −20 to 340° C. and is more preferably carried out at a temperature in the range from 20 to 180° C.

The reaction is preferably carried out at a total pressure in the range from 1 to 100 bar.

The reaction is preferably carried out in a molar ratio for the alcohol or alkylene oxide component to the phosphinic acid source (I) or alkylphosphonous acid (II) or monofunctionalized dialkylphosphinic acid (III) ranging from 10 000:1 to 0.001:1 and more preferably from 1000:1 to 0.01:1.

The reaction is preferably carried out in a molar ratio for the phosphinic acid source (I) or alkylphosphonous acid (II) or monofunctionalized dialkylphosphinic acid (III) to the solvent ranging from 1:10 000 to 1:0 and more preferably in a phosphinic acid/solvent molar ratio ranging from 1:50 to 1:1.

The amino functionality of the monofunctionalized dialkylphosphinic acids, their salts and esters of formula (III) can subsequently be reacted with mineral acids, carboxylic acids, Lewis acids, organic acids or mixtures thereof to form further ammonium salts.

The reaction is preferably carried out at a temperature of 0 to 150° C. and more preferably at a temperature of 20 to 70° C.

Suitable solvents are those used above in process stage a) of methods 1 to 4.

Preferred mineral acids are for example hydrochloric acid, sulfuric acid, nitric acid or phosphoric acid, phosphonic acid, phosphinic acid.

Preferred carboxylic acids are for example formic acid, acetic acid, propionic acid, butyric acid, lactic acid, palmitic acid, stearic acid, malonic acid, maleic acid, fumaric acid, tartaric acid, citric acid, ascorbic acid.

Preferred Lewis acids are boranes, for example diborane, trialkylborane, for example trimethylborane, triethylborane, tributylborane, triarylborane, for example triphenylborane.

It is particularly preferable for the ammonium salts to comprise salts of the abovementioned monoamino-functionalized dialkylphosphinic acids, their salts and esters with hydrochloric acid, phosphoric acid, phosphonic acid, phosphinic acid, acetic acid, citric acid, ascorbic acid, triphenylborane.

The monofunctionalized dialkylphosphinic acid or salt (III) can thereafter in stage c) be converted into further metal salts.

The metal compounds which are used in process stage c) preferably comprise compounds of the metals Ca, Al, Sb, Sn, Ge, Ti, Fe, Zr, Zn, Ce, Bi, Sr, Mn, Li, Na, K, more preferably Ca, Al, Ti, Zn, Sn, Ce, Fe.

Suitable solvents for process stage c) are those used above in process stage a).

The reaction of process stage c) is preferably carried out in an aqueous medium.

Process stage c) preferably comprises reacting the monofunctionalized dialkylphosphinic acids, esters and/or alkali metal salts (Ill) obtained after process stage b) with metal compounds of Mg, Ca, Al, Zn, Ti, Sn, Zr, Ce or Fe to form the monofunctionalized dialkylphosphinic acid salts (III) of these metals.

The reaction is carried out in a molar ratio of monofunctionalized dialkylphosphinic acid, ester or salt (Ill) to metal in the range from 8:1 to 1:3 (for tetravalent metal ions or metals having a stable tetravalent oxidation state), from 6:1 to 1:3 (for trivalent metal ions or metals having a stable trivalent oxidation state), from 4:1 to 1:3 (for divalent metal ions or metals having a stable divalent oxidation state) and from 3:1 to 1:4 (for monovalent metal ions or metals having a stable monovalent oxidation state).

Preferably, monofunctionalized dialkylphosphinic acid, ester or salt (III) obtained in process stage b) of the methods 1 to 4 is converted into the corresponding dialkylphosphinic acid and the latter is reacted in process stage c) with metal compounds of Mg, Ca, Al, Zn, Ti, Sn, Zr, Ce or Fe to form the monofunctionalized dialkylphosphinic acid salts (Ill) of these metals.

Preferably, monofunctionalized dialkylphosphinic acid/ester (Ill) obtained in process stage b) of the methods 1 to 4 is converted to a dialkylphosphinic acid alkali metal salt and the latter is reacted in process stage c) with metal compounds of Mg, Ca, Al, Zn, Ti, Sn, Zr, Ce or Fe to form the monofunctionalized dialkylphosphinic acid salts (III) of these metals.

The metal compounds of Mg, Ca, Al, Zn, Ti, Sn, Zr, Ce or Fe for process stage c) preferably comprise metals, metal oxides, hydroxides, oxide hydroxides, borates, carbonates, hydroxocarbonates, hydroxocarbonate hydrates, mixed metal hydroxocarbonates, mixed metal hydroxocarbonate hydrates, phosphates, sulfates, sulfate hydrates, hydroxosulfate hydrates, mixed metal hydroxosulfate hydrates, oxysulfates, acetates, nitrates, fluorides, fluoride hydrates, chlorides, chloride hydrates, oxychlorides, bromides, iodides, iodide hydrates, carboxylic acid derivatives and/or alkoxides.

The metal compounds preferably comprise aluminum chloride, aluminum hydroxide, aluminum nitrate, aluminum sulfate, titanyl sulfate, zinc nitrate, zinc oxide, zinc hydroxide and/or zinc sulfate.

Also suitable are aluminum metal, fluoride, hydroxychloride, bromide, iodide, sulfide, selenide; phosphide, hypophosphite, antimonide, nitride; carbide, hexafluorosilicate; hydride, calcium hydride, borohydride; chlorate; sodium aluminum sulfate, aluminum potassium sulfate, aluminum ammonium sulfate, nitrate, metaphosphate, phosphate, silicate, magnesium silicate, carbonate, hydrotalcite, sodium carbonate, borate, thiocyanate oxide, oxide hydroxide, their corresponding hydrates and/or polyaluminum hydroxy compounds, which preferably have an aluminum content of 9 to 40% by weight.

Also suitable are aluminum salts of mono-, di-, oligo-, polycarboxylic acids such as, for example, aluminum diacetate, acetotartrate, formate, lactate, oxalate, tartrate, oleate, palmitate, stearate, trifluoromethanesulfonate, benzoate, salicylate, 8-oxyquinolate.

Likewise suitable are elemental, metallic zinc and also zinc salts such as for example zinc halides (zinc fluoride, zinc chlorides, zinc bromide, zinc iodide).

Also suitable are zinc borate, carbonate, hydroxide carbonate, silicate, hexafluorosilicate, stannate, hydroxide stannate, magnesium aluminum hydroxide carbonate; nitrate, nitrite, phosphate, pyrophosphate; sulfate, phosphide, selenide, telluride and zinc salts of the oxoacids of the seventh main group (hypohalites, halites, halates, for example zinc iodate, perhalates, for example zinc perchlorate); zinc salts of the pseudohalides (zinc thiocyanate, zinc cyanate, zinc cyanide); zinc oxides, peroxides, hydroxides or mixed zinc oxide hydroxides. Preference is given to zinc salts of the oxoacids of transition metals (for example zinc chromate(VI) hydroxide, chromite, molybdate, permanganate, molybdate).

Also suitable are zinc salts of mono-, di-, oligo-, polycarboxylic acids, for example zinc formate, acetate, trifluoroacetate, propionate, butyrate, valerate, caprylate, oleate, stearate, oxalate, tartrate, citrate, benzoate, salicylate, lactate, acrylate, maleate, succinate, salts of amino acids (glycine), of acidic hydroxyl functions (zinc phenoxide etc), zinc p-phenolsulfonate, acetylacetonate, stannate, dimethyldithiocarbamate, trifluoromethanesulfonate.

Suitable metal compounds are salts of an element of the first main group, preferably an alkali metal hydroxide, alkali metal oxide hydroxide, alkali metal hydroxide carbonate, alkali metal alkoxide, more preferably lithium hydroxide, sodium hydroxide, potassium hydroxide, sodium methoxide, sodium ethoxide, sodium n-propoxide, sodium i-propoxide, sodium n-butoxide, sodium i-butoxide, sodium tert-butoxide, sodium amylate and/or sodium glycolate.

Suitable metal compounds are salts of an element of the second main and transition groups, preferably alkaline earth metal hydroxide, alkaline earth metal oxide hydroxide, alkaline earth metal hydroxide carbonate, more preferably magnesium hydroxide (Magnifin® H5, Albermarle), hydrotalcites ($Mg_6Al_2(OH)_{16}CO_3 \cdot nH_2O$), dihydrotalcite, magnesium carbonates or magnesium calcium carbonates, calcium hydroxide.

In the case of titanium compounds, metallic titanium is as is titanium(III) and/or (IV) chloride, nitrate, sulfate, formate, acetate, bromide, fluoride, oxychloride, oxysulfate, oxide, n-propoxide, n-butoxide, isopropoxide, ethoxide, 2-ethylhexyl oxide.

Also suitable is metallic tin and also tin salts (tin(II) and/or (IV) chloride); tin oxides and tin alkoxide such as, for example, tin(IV) tert-butoxide.

Cerium(III) fluoride, chloride and nitrate are also suitable.

In the case of zirconium compounds, metallic zirconium is preferred as are zirconium salts such as zirconium chloride, zirconium sulfate, zirconyl acetate, zirconyl chloride. Zirconium oxides and also zirconium (IV) tert-butoxide are also preferred.

The reaction in process stage c) is carried out at a solids content of the monofunctionalized dialkylphosphinic acid salts in the range from 0.1% to 70% by weight, preferably 5% to 40% by weight.

The reaction in process stage c) is preferably carried out at a temperature of 20 to 250° C., preferably at a temperature of 80 to 120° C.

The reaction in process stage c) is preferably carried out at a pressure between 0.01 and 1000 bar, preferably 0.1 to 100 bar.

The reaction in process stage c) preferably takes place during a reaction time in the range from $1*10^{-7}$ to 1000 h.

Preferably, the monofunctionalized dialkylphosphinic acid salt (III) removed after process stage c) from the reaction mixture by filtration and/or centrifugation is dried.

Preferably, the product mixture obtained after process stage b) is reacted with the metal compounds without further purification.

Preferred solvents are the solvents mentioned in process step a).

The reaction in process stage b) and/or c) is preferably carried out in the solvent system given by stage a).

The reaction in process stage c) is preferred in a modified given solvent system. Acidic components, solubilizers, foam inhibitors, etc are added for this purpose.

In a further embodiment of the method, the product mixture obtained after process stage a) and/or b) is worked up.

In a further embodiment of the method, the product mixture obtained after process stage b) is worked up and thereafter the monofunctionalized dialkylphosphinic acids and/or salts or esters (III) obtained after process stage b) are reacted in process stage c) with the metal compounds.

Preferably, the product mixture after process stage b) is worked up by isolating the monofunctionalized dialkylphosphinic acids and/or salts or esters (III) by removing the solvent system, for example by evaporation.

Preferably, the monofunctionalized dialkylphosphinic acid salt (III) of the metals Mg, Ca, Al, Zn, Ti, Sn, Zr, Ce or Fe selectively has a residual moisture content of 0.01% to 10% by weight, preferably of 0.1% to 1% by weight, an average particle size of 0.1 to 2000 μm, preferably of 10 to 500 μm, a bulk density of 80 to 800 g/l, preferably 200 to 700 g/l, and a Pfrengle flowability of 0.5 to 10, preferably of 1 to 5.

The molded articles, films, threads and fibers more preferably contain from 5% to 30% by weight of the monofunctionalized dialkylphosphinic acid/ester/salts produced according to one or more of claims 1 to 15, from 5% to 80% by weight of polymer or mixtures thereof, from 5% to 40% by weight of additives and from 5% to 40% by weight of filler, wherein the sum total of the components is always 100% by weight.

The additives preferably comprise antioxidants, antistats, blowing agents, further flame retardants, heat stabilizers, impact modifiers, processing aids, lubricants, light stabilizers, antidripping agents, compatibilizers, reinforcing agents, nucleus-forming agents, nucleating agents, additives for laser marking, hydrolysis stabilizers, chain extenders, color pigments, softeners, plasticizers and/or plasticizing agents.

Preference is given to a flame retardant containing 0.1 to 90% by weight of the low-halogen monofunctionalized dialkylphosphinic ester and 0.1% to 50% by weight of further additives, more preferably diols.

Preferred additives are also aluminum trihydrate, antimony oxide, brominated aromatic or cycloaliphatic hydrocarbons, phenols, ethers, chloroparaffin, hexachlorocyclopentadiene adducts, red phosphorus, melamine derivatives, melamine cyanurates, ammonium polyphosphates and magnesium hydroxide. Preferred additives are also further flame retardants, more particularly salts of dialkylphosphinic acids.

More particularly, the present invention provides for the use of the present invention monofunctionalized dialkylphosphinic acid, esters and salts (III) as flame retardants or as an intermediate in the manufacture of flame retardants for thermoplastic polymers such as polyesters, polystyrene or polyamide and for thermoset polymers such as unsaturated polyester resins, epoxy resins, polyurethanes or acrylates.

Suitable polyesters are derived from dicarboxylic acids and their esters and diols and/or from hydroxycarboxylic acids or the corresponding lactones. It is preferable to use terephthalic acid and ethylene glycol, 1,3-propanediol and 1,3-butanediol.

Suitable polyesters include inter alia polyethylene terephthalate, polybutylene terephthalate (Celanex® 2500, Celanex® 2002, from Celanese; Ultradur®, from BASF), poly-1,4-dimethylolcyclohexane terephthalate, polyhydroxybenzoates, and also block polyether esters derived from polyethers having hydroxyl end groups; and also polyesters modified with polycarbonates or MBS.

Synthetic linear polyesters having permanent flame retardancy are composed of dicarboxylic acid components, $C_2$-$C_6$-diol components of the present invention monofunctionalized dialkylphosphinic acids and ester, and of the monofunctionalized dialkylphosphinic acids and esters produced by the method of the present invention as phosphorus-containing chain members. The monofunctionalized dialkylphosphinic acids and esters of the invention are part of the polymer chain. The phosphorus-containing chain members account for 2-20% by weight of the dicarboxylic acid component of the polyester. The resulting phosphorus content in the polymer is preferably 0.1-5% by weight, more preferably 0.5-3% by weight.

Preference is given to adding the monomeric monofunctionalized dialkylphosphinic acid and ester to dicarboxylic acid components, $C_2$-$C_6$ diol components and then esterifying/transesterifying and polycondensing.

Preferably, the flame-retardant molding material is produced from the free dicarboxylic acid and diols by initially esterifying directly and then polycondensing to a non-flame-retardant precondensate.

When proceeding from dicarboxylic esters, more particularly dimethyl esters, it is preferable to first transesterify and then to polycondense to a non-flame-retardant precondensate by using catalysts customary for this purpose.

Preferably, it is at this stage that the monomeric monofunctionalized dialkylphosphinic acid and ester (III) is added and the polymerization completed. The monomeric monofunctionalized dialkylphosphinic acid, ester will then preferably have been randomly incorporated into the polymer chain between the dicarboxylic acid diglycol units.

Polyester production may preferably proceed by adding customary additives (crosslinking agents, matting agents and stabilizing agents, nucleating agents, dyes and fillers, etc) in addition to the customary catalysts.

The ratio of dicarboxylic esters to diol components used for esterification and/or transesterification is preferably in the range from 1:1 to 1:3 mol/mol.

Preferred dicarboxylic acids are aromatic acids such as terephthalic acid, isophthalic acid, 5-sulfoisophthalic acid, biphenyl-para-dicarboxylic acid and para-phenylenediacetic acid.

Preference is further given to naphthalenedicarboxylic acids such as 1,3-naphthalenedicarboxylic acid, 1,4-naphthalenedicarboxylic acid, 1,5-naphthalenedicarboxylic acid, 2,6-naphthalenedicarboxylic acid, 2,7-naphthalenedicarboxylic acid; saturated aliphatic dicarboxylic acids such as oxalic acids, malonic acid, succinic acid, glutaric acid, adipic acid, pimelic acid, suberic acid, azelaic acid, sebacic acid, decanedicarboxylic acid, dodecanedicarboxylic acid, tetradecanedicarboxylic acid, hexadecanedicarboxylic acid, 1,3-cyclobutanedicarboxylic acid, 1,3-cyclopentanedicarboxylic acid, 1,2-cyclohexanedicarboxylic acid, 1,3-cyclohexanedicarboxylic acid, 1,4-cyclohexanedicarboxylic acid and 2,5-norbornanedicarboxylic acid; unsaturated aliphatic dicarboxylic acid such as fumaric acid, maleic acid, itaconic acid.

Preferred alkylene glycols are ethylene glycol, 1,3-propanediol, 1,4-butanediol and higher homologs, diethylene glycol, triethylene glycol, neopentyl glycol, 1,2-cyclohexanediol, 1,3-cyclohexanediol, 1,4-cyclohexanediol, 1,2-cyclohexanedimethanol, 1,3-cyclohexanedimethanol, 1,4-cyclohexanedimethanol, 1,4-cyclohexanediethanol, 1,10-decamethyleneglycol, 1,12-dodecanediol, polyethylene glycol, polytrimethylene glycol and polytetramethylene glycol; aromatic glycols such as hydroquinone, 4,4'-dihydroxybisphenol, 1,4-bis(hydroxyethoxy)benzenes, 1,4-bis(hydroxyethoxyphenyl) sulfone, bis(p-hydroxyphenyl) ether, bis(p-hydroxyphenyl) sulfone, bis(p-hydroxyphenyl)methane, 1,2-bis(p-hydroxyphenyl)ethane, bisphenol A, bisphenol C, 2,5-naphthalenediol.

Preference is further given to polyesters based on hydroxy carboxylic acids such as lactic acid, citric acid, tartaric acid, hydroxyacetic acid, 3-hydroxybutyric acid, p-hydroxybenzoic acid, p-(2-hydroxyethoxy)benzoic acid and 4-hydroxycyclohexanecarboxylic acid.

The esterification and/or transesterification involved in polyester production is preferably carried out at temperatures of 100-300° C., more preferably at 180-240° C.

The polycondensation involved in polyester production preferably takes place at pressures between 0.1 to 200 mbar and temperatures of 150-450° C., more preferably at 200-300° C.

It is further preferable to condense the monofunctionalized dialkylphosphinic acids and esters (III) to initially form an oligomer of the formula $X—O—(P(=O)R—CH_2—O)_n—H$ where $R=C_1$-$C_8$-alkyl, $C_6$-$C_{20}$-alkaryl, $C_6$-$C_{20}$-aralkyl, $C_6$-$C_{20}$-aryl and X=alkyl, hydroxyalkyl, alkaryl, H and also n=2.0 to 100.

A further embodiment is a composition comprising monomer 10-75 mol %, dimer 10-75 mol % and trimer 0 to 35 mol %.

Preference is given to adding the oligomer to dicarboxylic acid components, $C_2$-$C_6$ diol components and then to esterify/transesterify and polycondense. Preference is then given to phosphorus concentrations in the range from 0.1% to 5% by weight.

Preferably, this oligomer is then mixed with precondensate and the polycondensation is completed. Preference is then given to phosphorus concentrations in the range from 0.1% to 5% by weight.

It is further preferable to mix monomeric monofunctionalized dialkylphosphinic acid or ester (Ill) or oligomer to fully condensed polyester under condensation conditions (0.01 to 1000 mbar, 140-350° C., 0.5-3 h). Preference is then given to phosphorus concentrations in the range from 0.1% to 5% by weight.

Preference is further given to condensing monomeric or oligomeric monofunctionalized dialkylphosphinic acid or ester (Ill) with prepolymer to form a masterbatch/concentrate. Preference is then given to phosphorus concentrations in the range from 0.1% to 25% by weight and more preferably in the range from 1% to 10% by weight.

Preferably, the masterbatch is mixed with non-flame-retardant polymer under extrusion conditions. Preferred polymers are polyethylene terephthalate, polytrimethylene terephthalate and polybutylene terephthalate, polyamides.

The advantage of using masterbatches is that the addition of increased amounts of monofunctionalized dialkylphosphinic acid, ester, salts (Ill) does not result in fluctuations in the melt viscosity of the flame-retardant polymeric molding material, as can be the case on adding other flame retardants to precondensate. Fluctuations in the melt viscosity make it difficult to control the melt viscosity.

The flame-retardant polyester molding materials produced according to the present invention are preferably used in flame-retardant polyester molded articles.

Preferred flame-retardant polyester molded articles are threads, fibers, self-supporting films/sheets and molded articles containing mainly terephthalic acid as dicarboxylic acid component and mainly ethylene glycol as diol component.

The resulting phosphorus content in threads and fibers produced from flame-retardant polyesters is preferably 0.1%-18%, more preferably 0.5%-15% by weight and in the case of self-supporting films/sheets 0.2%-15%, preferably 0.9%-12% by weight.

Preference is given to a flame-retardant polymeric molding material in which the polycondensation product contains at least one alkyldicarboxylic acid, at least one diamine and a monofunctionalized dialkylphosphinic acid. The polyamide thus rendered flame-retardant contains from 0.1% to 1% of phosphorus. The monofunctionalized dialkylphosphinic acid or ester (III) is preferably added to the monomeric salts under condensation conditions and cocondensed into the polymer. It will then be randomly incorporated into the monomer sequence of alkyldicarboxylic acid-diamine.

Suitable polystyrenes are polystyrene, poly(p-methylstyrene) and/or poly(alpha-methylstyrene).

Suitable polystyrenes preferably comprise copolymers of styrene or alpha-methylstyrene with dienes or acrylic derivatives, for example styrene-butadiene, styrene-acrylonitrile, styrene-alkyl methacrylate, styrene-butadiene-alkyl acrylate and styrene-butadiene-alkyl methacrylate, styrene-maleic anhydride, styrene-acrylonitrile-methyl acrylate; mixtures of high impact strength from styrene copolymers and another polymer, for example a polyacrylate, a diene polymer or an ethylene-propylene-diene terpolymer; also block copolymers of styrene, for example styrene-butadiene-styrene, styrene-isoprene-styrene, styrene-ethylene/butylene-styrene or styrene-ethylene/propylene-styrene.

Suitable polystyrenes preferably also comprise graft copolymers of styrene or of alpha-methylstyrene, for example styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene-propylene-diene terpolymers, styrene and acrylonitrile on poly(alkyl acrylate)s or poly(alkyl methacrylate)s, styrene and acrylonitrile on acrylate-butadiene copolymers, and also their mixtures, as are known for example as ABS, MBS, ASA or AES polymers.

The polymers preferably also comprise polyamides and copolyamides derived from diamines and dicarboxylic acids and/or from aminocarboxylic acids or the corresponding lactams, such as nylon-2,12, nylon-4, nylon-4,6, nylon-6, nylon-6,6, nylon-6,9, nylon-6,10, nylon-6,12, nylon-6,66, nylon-7,7, nylon-8,8, nylon-9,9, nylon-10,9, nylon-10,10, nylon-11, nylon-12, and so on. Such polyamides are known for example under the trade names Nylon®, from DuPont, Ultramid®, from BASF, Akulon® K122, from DSM, Zytel® 7301, from DuPont; Durethan® B 29, from Bayer and Grillamid®, from Ems Chemie, inter alia.

Also suitable are aromatic polyamides proceeding from m-xylene, diamine and adipic acid; polyamides produced from hexamethylenediamine and iso- and/or terephthalic acid and optionally an elastomer as modifier, for example poly-2,4,4-trimethylhexamethyleneterephthalamide or poly-m-phenyleneisophthalamide, block copolymers of the aforementioned polyamides with polyolefins, olefin copolymers, ionomers or chemically bonded or grafted elastomers or with polyethers, for example with polyethylene glycol, polypropylene glycol or polytetramethylene glycol. Also EPDM- or ABS-modified polyamides or copolyamides; and also polyamides condensed during processing ("RIM polyamide systems").

The monofunctionalized dialkylphosphinic acid/ester/salts produced according to one or more of claims 1 to 15 are preferably used in molding materials further used for producing polymeric molded articles.

It is particularly preferable for the flame-retardant molding material to contain from 5% to 30% by weight of monofunctionalized dialkylphosphinic acids, salts or esters produced according to one or more of claims 1 to 15, from 5% to 80% by weight of polymer or mixtures thereof, from 5% to 40% by weight of additives and 5% to 40% by weight of filler, wherein the sum total of the components is always 100% by weight.

The present invention also provides flame retardants containing monofunctionalized dialkylphosphinic acids, salts or esters produced according to one or more of claims 1 to 15.

The present invention also provides polymeric molding materials and also polymeric molded articles, films, threads and fibers containing the monofunctionalized dialkylphosphinic acid salts of the metals Mg, Ca, Al, Zn, Ti, Sn, Zr, Ce or Fe produced according to the present invention.

The invention more particularly provides for the use of the monofunctionalized dialkylphosphinic acid salts obtained according to the present invention as flame retardants for thermoplastic polymers or as an intermediate stage in the manufacture of flame retardants for polyesters, polystyrene or polyamide and for thermoset polymers such as unsaturated polyester resins, epoxy resins, polyurethanes or acrylates.

The examples which follow illustrate the invention.

Production, processing and testing of flame-retardant polymeric molding materials and flame-retardant polymeric molded articles.

The flame-retardant components are mixed with the polymeric pellets and any additives and incorporated on a twin-screw extruder (Leistritz LSM® 30/34) at temperatures of 230 to 260° C. (glassfiber-reinforced PBT) or of 260 to 280° C. (glassfiber-reinforced PA 66). The homogenized polymeric strand was hauled off, water bath cooled and then pelletized.

After sufficient drying, the molding materials were processed on an injection molding machine (Aarburg Allrounder) at melt temperatures of 240 to 270° C. (glassfiber-reinforced PBT) or of 260 to 290° C. (glassfiber-reinforced PA 66) to give test specimens. The test specimens are subsequently flammability tested and classified using the UL 94 (Underwriter Laboratories) test.

UL 94 (Underwriter Laboratories) fire classification was determined on test specimens from each mixture, using test specimens 1.5 mm in thickness.

The UL 94 fire classifications are as follows:

V-0: Afterflame time never longer than 10 sec, total of afterflame times for 10 flame applications not more than 50 sec, no flaming drops, no complete consumption of the specimen, afterglow time for specimens never longer than 30 sec after end of flame application.

V-1: Afterflame time never longer than 30 sec after end of flame application, total of afterflame time for 10 flame applications not more than 250 sec, afterglow time for specimens never longer than 60 sec after end of flame application, other criteria as for V-0

V-2: Cotton indicator ignited by flaming drops, other criteria as for V-1 Not classifiable (ncl): does not comply with fire classification V-2.

Some investigated specimens were also tested for their LOI value. The LOI (Limiting Oxygen Index) value is determined according to ISO 4589. According to ISO 4589, the LOI is the lowest oxygen concentration in volume percent which in a mixture of oxygen and nitrogen will support combustion of the plastic. The higher the LOI value, the greater the flammability resistance of the material tested.

| LOI | 23 | flammable |
| --- | --- | --- |
| LOI | 24-28 | potentially flammable |
| LOI | 29-35 | flame resistant |
| LOI | >36 | particularly flame-resistant |

EXAMPLE 1

At room temperature, a three-neck flask equipped with stirrer and high-performance condenser is initially charged with 295 g of water and this initial charge is "devolatilized" by stirring and passing nitrogen through it for 10 minutes. Then, 0.3 mg of palladium(II) sulfate and 3.6 mg of tris(3-sulfophenyl)phosphine trisodium salt are added and the mixture is stirred for a further 15 minutes. 103.4 g of phosphinic acid are then added, while stirring to 103.4 g of water. The reaction solution is transferred to a 2 l Büchi reactor and charged with 2.5 bar ethylene while stirring and the reaction mixture is heated to 80° C. After 44 g of ethylene has been taken up, the system is cooled down to room temperature and free ethylene is discharged with combustion. The reaction mixture is freed of solvent on a rotary evaporator at not more than 60° C. The residue is admixed with 160 g of VE water and at room temperature stirred for 1 hour under nitrogen. The residue obtained is filtered and the filtrate is extracted with 100 ml of toluene. The aqueous phase is freed of solvent on a rotary evaporator to obtain 147.2 g of ethylphosphonous acid (96.3%). This acid is placed with 147 g of demineralized water and 47.6 g of paraformaldehyde (95%) in a laboratory autoclave from Berghoff. After stirring at 150° C. for six hours, the crude product is evaporated in the Rotavapor to obtain 189.5 g of ethylhydroxymethylphosphinic acid (91.8% 31P NMR). This corresponds to a yield of 93%.

EXAMPLE 2

14.6 g of ethylphosphonous acid (prepared according to example 1) are admixed with 21.2 g of water, 207.3 g of ethanol and 35.0 g of benzaldehyde and heated in a multi-neck round-bottom flask with fitted KPG stirrer, thermometer and reflux condenser at 110° C. for 6 h. The reaction solution is found by 31P NMR spectroscopy to contain 65 mol % of ethylhydroxymethylphenylphosphinic acid.

EXAMPLE 3

48.8 g of ethylphosphonous acid (prepared according to example 1) are admixed with 43 g of water and 26.4 g of paraldehyde and heated in a Berghoff laboratory autoclave at 150° C. for 12 h. The reaction solution is found by 31P NMR spectroscopy to contain 77 mol % of ethylhydroxyethylphenylphosphinic acid.

EXAMPLE 4

As in example 1, a Berghoff laboratory autoclave is charged with 100.1 g of ethylphosphonous acid (96.3%) (prepared according to example 1), 100.1 g of demineralized water and 34.0 g of paraformaldehyde (95%). After stirring at 170° C. for six hours, the crude product is evaporated in the Rotavapor and thereafter reacted with 88.7 g of ethylene oxide in a three-neck round-bottom flask with fitted KPG stirrer, reflux condenser and gas inlet tube to obtain 229.5 g of glycol ester having a phosphorus content of 14.9% and a 31P NMR signal at about 59 ppm. The level of free glycol is 4%.

EXAMPLE 5

A three-neck round-bottom flask with fitted KPG stirrer, reflux condenser and dropping funnel is initially charged with 44.0 g of paraformaldehyde (95%), 105.5 g of demineralized water and 233.4 g of diethylamine hydrochloride, followed by the addition of 100.1 g of ethylphosphonous acid (96.3%) (prepared according to example 1) during 6 h at 110° C. with stirring. The pH of the reaction solution is adjusted to below 1 with 8 g of 37% hydrochloric acid. After one hour of refluxing, a solution of ethyldiethylaminomethylphosphinic acid is obtained.

EXAMPLE 6

A 4 l three-neck flask fitted with KPG stirrer, reflux condenser and dropping funnel is initially charged with 1094 g of demineralized water, 502.1 g of ethyldiethylaminomethylphosphinic acid (prepared according to example 5), followed by heating to 90° C. During 2 h, 224 g of an aqueous aluminum sulfate solution (4.3% Al) are added dropwise with stirring. The precipitated solid material is filtered off, washed with 1000 g of demineralized water and then dried at 130° C. to obtain 182 g of aluminum tris(bisdiethylaminomethylphosphinate) corresponding to a yield of 91%.

EXAMPLE 7

A one-liter three-neck flask with fitted reflux condenser, KPG cooler and dropping funnel is charged with 48.8 g of ethylphosphonous acid (96.3%) (prepared according to example 1) and 22.0 g of paraldehyde (acetaldehyde trimer) in 125 g of water, and this charge is heated to reflux under nitrogen. Then, a solution of 109.9 g of diphenylmethylamine hydrochloride in 250 g of demineralized water is added dropwise. The mixture is subsequently stirred for 2 h and cooled, and the solid material is filtered off, washed with acetone and dried. Yield: 132 g of diphenylmethylaminephosphinic acid (87%).

EXAMPLE 8

132 g of diphenylmethylaminophosphinic acid (prepared according to example 7) are admixed with 715 g of 20% sulfuric acid and refluxed for 2 h. This is followed by evaporating to dryness, washing twice with 100 g of diisopropyl ether and a further evaporation. The residue is taken up with ethanol and admixed with propylene oxide. The precipitated solid material is filtered off, washed with ethanol and dried to obtain 56 g of (1-amino-1-methyl)methylethylphosphinic acid in 87% yield.

EXAMPLE 9

In a one-liter three-neck flask with fitted reflux condenser, KPG cooler and dropping funnel, a solution of 49.3 g of ethylphosphonous acid (96.3%) (prepared according to example 1) in 125 g of water is added dropwise under nitrogen to a refluxing solution of 91.6 g of diphenylmethylamine, 22.0 g of paraldehyde (acetaldehyde trimer) and 25 g of 98% sulfuric acid in 250 g of demineralized water. The mixture is subsequently stirred for 2 h and cooled down, and the solid material is filtered off, washed with acetone and dried to obtain 125 g of diphenylmethylaminiphosphinic acid in a yield of 82%.

EXAMPLE 10

405.5 g of ethylhydroxymethylphosphinic acid (prepared according to example 1) are admixed with 1115 g of butanol and the water of condensation is removed with a water trap by boiling at atmospheric pressure. After the esterification has ended, the butanol is separated off in vacuo and the residue is vacuum distilled via a Vigreux column to obtain 392 g of n-butyl ethylhydroxymethylphosphinate in a 79% yield.

EXAMPLE 11

Ethylphosphonous acid is prepared in the first step as in example 1. Butanol is added to convert it into the n-butyl ethylphosphonite ester similarly to example 10. In a second step, with stirring and cooling to a maximum of 60° C., 37.5 g of n-butyl ethylphosphonite and 10.8 g of vinyl acetate are initially charged and a solution of 0.6 g of sodium butoxide in 20 g of butanol is added. The reaction solution is distilled under reduced pressure (0.5 mmHg) to obtain 23 g of n-butyl ethyl-(1-hydroxyethyl acetate)phosphinate ($C_2H_5$—P(O)(O-n-$C_4H_9$)—CH(O—$COCH_3$)—$CH_3$). This ester is reacted with 9.9 g of concentrated sulfuric acid and 6.7 g of demineralized water in 100 g of methanol to obtain 17.2 g of n-butyl ethyl-(1-hydroxyethyl)phosphinate.

EXAMPLE 12

1000 g of dimethylterephtalate and 800 g of ethylene glycol are heated in an autoclave together with 230 mg of manganese(II) acetate tetrahydrate up to 220° C. and the resulting methanol is distilled off. Then, 72 g of a glycol ester obtained according to example 4 and also 400 mg of antimony trioxide and 400 mg of phosphoric acid are added, and the mixture is first heated to 250° C. at 1 Torr pressure and then to 275° C. at 0.2 Torr pressure to obtain a flame-retardant polyester molding material having a phosphorus content of about 1% which achieves a V-0 classification.

EXAMPLE 13

The ester of example 10 is admixed with 3 g of dibutyltin laurate (catalyst), and heated to 180° C., in a 1 l jacketed stirred reactor. The pressure is reduced to 1 mmHg during 14 h. The product obtained (231 g) is an internal homo-oligomer of ethylhydroxymethylphosphinic acid, formed by elimination of butanol, and has a phosphorus content of 29.2% (th 29.2%). In a 1 l autoclave, 200 g of the homo-oligomer thus obtained are melted with 450 g of PET chips (Polyclear 1101, from KoSa) at 290° C. and 100 mmHg for 0.5 h with stirring. This is followed by cooling. The flame-retardant polymer obtained has a phosphorus content of 9%, is processed into UL test specimens and achieves a V-0 classification.

EXAMPLE 14

A twin-screw compounder is used to compound 8960 g of a non-flame-retardant PBT pellet material with 1040 g of an oligomer according to example 13 at 275° C. to form flame-retardant PBT pellets. The pellets had a phosphorus content of 3.0% and achieves a V-0 classification.

| Ex. | R—P(=O)(OX)—H [g] | Solvent Type | Solvent [g] | C=X compound Type | C=X compound [g] | Component 2 Type | Component 2 [g] | Product [g] |
|---|---|---|---|---|---|---|---|---|
| 1 | 147.2 | water | 147.2 | formaldehyde | 47.6 | — | — | 189.5 |
| 2 | 14.6 | water/ethanol | 21.2/207.3 | benzaldehyde | 35.0 | — | — | — |
| 3 | 48.8 | water | 43.0 | acetaldehyde | 26.4 | — | — | — |
| 4 | 100.1 | water | 100.1 | formaldehyde | 34.0 | ethylene oxide | 88.7 | 229.5 |
| 5 | 100.1 | water | 105.5 | formaldehyde | 44.0 | diethylamine | 233.4 | — |
| 7 | 48.8 | water | 375.0 | acetaldehyde | 22.0 | diphenyl-methylamine | 91.6 | 132.0 |
| 9 | 48.8 | water | 375.0 | acetaldehyde | 22.0 | diphenyl-methylamine | 91.6 | 125.0 |
| 11 | 37.5 | butanol | 20.0 | vinyl acetate | 10.8 | — | — | 23.0 |

What is claimed is:

1. A method for producing monofunctionalized dialkylphosphinic acids, esters or salts comprising the steps of:

a) reacting a phosphinic acid source (I)

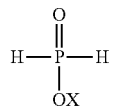

(I)

with olefins (IV)

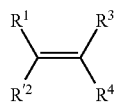

(IV)

in the presence of at least one catalyst A to form an alkylphosphonous acid, salt or ester (II)

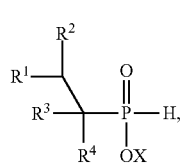

(II)

b) reacting the alkylphosphonous acid, salt or ester (II) with one or more compounds C=C, C=O or C=N, wherein compounds C=O are ketones of the type $R^5R^6C=O$ or aldehydes of the type $R^5CHO$, wherein compounds C=C are selected from the group consisting of vinyl acetate, vinyl propionate, vinyl butyrate, vinyl pivalate, vinyl benzoate, vinyl cinnamate, vinyl stearate, vinyl laurate, 1-propenyl acetate, 1-propenyl propionate, 1-propenyl butyrate, 1-propenyl pivalate, 1-propenyl benzoate, 1-propenyl cinnamate, 1-propenyl stearate, 1-propenyl laurate, 1-butenyl acetate, 1-butenyl propionate, 1-butenyl butyrate, 1-butenyl pivalate, 1-butenyl benzoate, 1-butenyl cinnamate, 1-butenyl stearate and 1-butenyl laurate to form a compound (III)

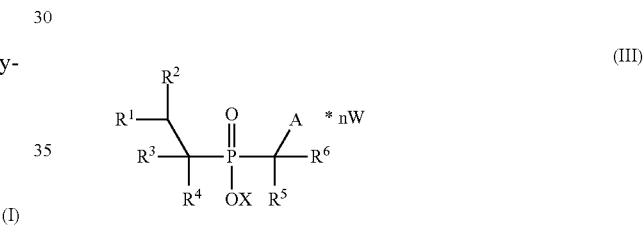

(III)

where $R^1$, $R^2$, $R^3$, $R^4$, $R^5$, $R^6$ are identical or different and are H, methyl, ethyl, n propyl, isopropyl, n-butyl, isobutyl, tert-butyl, phenyl CHO, OC(O)CH$_2$CN, CH(OH)C$_2$H$_5$, CH$_2$CH(OH)CH$_3$, 9-anthracene, 2-pyrrolidone, (CH$_2$)$_m$OH, (CH$_2$)$_m$SH, (CH$_2$)$_m$S-2-thiazoline, (CH$_2$)$_m$SiMe$_3$, CHR$^7$(CH$_2$)$_m$CH$_3$, C(O)R$^7$, (CH$_2$)$_m$C(O)R$^7$, CH=CHR$^7$, R$^5$R$^6$C=CHR$^7$, CH=CH—C(O)R$^7$, wherein R$^7$ is H, C$_1$-C$_8$-alkyl or C$_6$-C$_{18}$-aryl, m is an integer from 0 to 10 and X is H, n-butyl, isobutyl, tert-butyl, phenyl, ethylene glycol, propyl glycol, butyl glycol, pentyl glycol, hexyl glycol, allyl, glycerol (CH$_2$)$_k$OH, CH$_2$—CHOH—CH$_2$OH, (CH$_2$)$_k$O(CH$_2$)$_k$H, (CH$_2$)$_k$—CH(OH)—(CH$_2$)$_k$H, (CH$_2$—CH$_2$O)$_k$H, (CH$_2$—C[CH$_3$]HO)$_k$H, (CH$_2$—CH$_2$O)$_k$-alkyl, (CH$_2$—C[CH$_3$]HO)$_k$-alkyl, (CH$_2$—CH$_2$O)$_k$(CH$_2$—C[CH$_3$]HO)O-alkyl, (CH$_2$)$_k$—CH=CH(CH$_2$)$_k$H, (CH$_2$)$_k$NH$_2$ or (CH$_2$)$_k$N[(CH$_2$)$_k$H]$_2$, wherein k is an integer from 0 to 10, Mg, Ca, Al, Sb, Sn, Ge, Ti, Fe, Zr, Zn, Ce, Bi, Sr, Mn, Cu, Ni, Li, Na, K, H, a protonated nitrogen base or a combination thereof and wherein A is OH, NH$_2$, NHEt, NHCH(C$_6$H$_5$)$_2$ or O—CO—R$^8$ and R$^8$ has the same meanings as $R^1$ to $R^6$ and W is hydrochloric acid, sulfuric acid, nitric acid, phosphoric acid, phosphonic acid, phosphinic acid, formic acid, acetic acid, propionic acid, butyric acid, lactic acid, palmitic acid, stearic acid, malonic acid, maleic acid, fumaric acid, tartaric acid, citric acid, ascorbic acid, trimethylborane, triethylborane, tributylborane or triphenylborane, where n is an integer or fraction ranging from 0 to 4 and the at least one catalyst A is a transition metal, transition metal compound, a catalyst system including a transition metal, transition metal compound and at least one ligand or a combination thereof.

2. The method according to claim 1 wherein step b) further comprises reacting the alkylphosphonous acid, its salt or ester (II) first with compounds C═C, C═O or C═N and then with $H_2NEt$, $H_2NCH(C_6H_5)_2$, $NH_3$ or salts thereof.

3. The method according to claim 1 wherein step b) further comprises reacting the alkylphosphonous acid, its salt or ester (II) simultaneously with compounds comprising C═C, C═O or C═N and with $H_2NEt$, $H_2NCH(C_6H_5)_2$, $NH_3$ or salts thereof.

4. The method according to claim 1, wherein the monofunctionalized dialkylphosphinic acid, its salt or ester (III) obtained after step b) is reacted in a step c) with a metal compound of Mg, Ca, Al, Sb, Sn, Ge, Ti, Fe, Zr, Zn, Ce, Bi, Sr, Mn, Li, Na, K, a protonated nitrogen base or a combination thereof to form the monofunctionalized dialkylphosphinic acid salts (III) of these metals, of a nitrogen compound or a combination thereof.

5. The method according to claim 1, wherein the alkylphosphonous acid, salt or ester (II) obtained after step a), the monofunctionalized dialkylphosphinic acid, salt or ester (III) obtained after step b), the resulting reaction solution thereof or a combination thereof are esterified with an alkylene oxide or an alcohol M-OH, M'-OH or both, and the resulting alkylphosphonous ester (II), monofunctionalized dialkylphosphinic ester (III) or a combination thereof is subjected to the reaction step b).

6. The method according to claim 1, wherein X is H, Ca, Mg, Al, Zn, Ti, Fe, Ce.

7. The method according to claim 1, wherein the transition metal and transition metal compound are from the seventh or eighth transition groups.

8. The method according to claim 1, wherein the transition metal and transition metal compound are rhodium, nickel, palladium, platinum or ruthenium.

9. The method according to claim 1, wherein W is hydrochloric acid, sulfuric acid, nitric acid, phosphoric acid, phosphonic acid, phosphinic acid, formic acid, acetic acid, propionic acid, butyric acid, lactic acid, palmitic acid, stearic acid, malonic acid, maleic acid, fumaric acid, tartaric acid, citric acid, ascorbic acid, trimethylborane, triethylborane, tributylborane or triphenylborane.

10. The method according to claim 5, wherein the alcohol of the formula M-OH is a linear or branched, saturated or unsaturated, monohydric organic alcohol having a carbon chain length of $C_1$-$C_{18}$ and the alcohol of the general M'-OH is a linear or branched, saturated or unsaturated polyhydric organic alcohols having a carbon chain length of $C_1$-$C_{18}$.

11. The method according to claim 1, further comprising the step of separating —O—CO—$R^8$ from the monofunctionalized dialkylphosphinic acid, esters, or salts according to formula (III) when A is —O—CO—$R^8$, by acidic or alkaline hydrolysis using acids or bases in the presence of water and at least one catalyst B, wherein the at least one catalyst B is selected from the group consisting of metals, metal hydrides, metal hydroxides, metal alkoxides and combinations thereof.

12. The method according to claim 5, wherein the at least one catalyst B is lithium, lithium hydride, lithium aluminohydride, methyllithium, butyllithium, tertbutyllithium, lithium diisopropylamide, sodium, sodium hydride, sodium borohydride, sodium hydroxide, sodium methoxide, sodium ethoxide or sodium butoxide, potassium hydroxide, potassium methoxide, potassium ethoxide or potassium butoxide.

* * * * *